(12) United States Patent
Levicky et al.

(10) Patent No.: US 8,263,411 B2
(45) Date of Patent: Sep. 11, 2012

(54) CAPACITIVE MORPHOLINO DIAGNOSTICS FOR ANALYSIS OF NUCLEIC ACIDS

(75) Inventors: Rastislav Levicky, Irvington, NY (US); Napoleon Tercero, New York, NY (US); Kang Wang, Staten Island, NY (US); Ping Gong, Cambridge, MA (US); Kenneth Shepard, Ossining, NY (US)

(73) Assignee: Polytechnic Institute of NYU, Brooklyn, NY (US)

( * ) Notice: Subject to any disclaimer, the term of this patent is extended or adjusted under 35 U.S.C. 154(b) by 691 days.

(21) Appl. No.: 12/362,071

(22) Filed: Jan. 29, 2009

(65) Prior Publication Data

US 2010/0187133 A1 Jul. 29, 2010

(51) Int. Cl.
*G01N 33/50* (2006.01)
(52) U.S. Cl. ............... 436/94; 205/792; 536/24.1
(58) Field of Classification Search ............... 536/23.1, 536/24.1, 24.3, 24.5; 205/787, 792, 793.5; 204/403.01; 436/94
See application file for complete search history.

(56) References Cited

U.S. PATENT DOCUMENTS

| 2004/0146863 A1* | 7/2004 | Pisharody et al. | 435/6 |
| 2005/0146383 A1* | 7/2005 | Moore et al. | 331/57 |
| 2005/0181409 A1* | 8/2005 | Park et al. | 435/6 |

OTHER PUBLICATIONS

Summerton, J., et al., "Morpholino Antisense Oligomers: Design, Preparation, and Properties", vol. 7, 1997, pp. 187-195.*

* cited by examiner

*Primary Examiner* — J. Christopher Ball
(74) *Attorney, Agent, or Firm* — Laurence P. Colton; Smith Risley Tempel Santos LLC

(57) ABSTRACT

A method to monitor the progress of hybridization between nucleic acid strands in solution and Morpholino strands immobilized on a solid support such as a working electrode in-situ, in real-time, and using label-free electrochemical measurements sensitive to hybridization-induced changes in the near-surface dielectric constant and charge organization.

7 Claims, 11 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ttttaaattc tgcaagtgat                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2 ttttttttcct tccttttttt                                                 20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atcacttgca gaatttaa                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaagga aggaaaaa                                                    18

US 8,263,411 B2

CAPACITIVE MORPHOLINO DIAGNOSTICS FOR ANALYSIS OF NUCLEIC ACIDS

STATEMENT OF GOVERNMENT INTEREST

The project described was supported by Award Number R33HG003089 from the National Human Genome Research Institute of the United States National Institutes of Health.

BACKGROUND OF THE INVENTION

1. Technical Field

This invention relates generally to nucleic acid analysis and more specifically to the label-free DNA analysis by surface hybridization to morpholine monolayers.

2. Prior Art

Surface hybridization, in which sequence-specific binding between polynucleic acid "probes" on a solid support and complementary "targets" from solution occurs at a solid-liquid interface, was introduced as a diagnostic method in the 1960's[1,2]. The technique continues to be widely exploited in modern DNA microarray and biosensor technologies for genotyping, transcriptome profiling, genetic identification, and related diagnostic applications[3]. When hybridization occurs at a surface, experiments show that the phenomenology of the reaction is more complex than in solution[4-17]. The crowded interfacial environment is characterized by nucleotide concentrations that approach the molar range, and the resultant amplification of interactions between nucleotides can have a dramatic impact on physical behavior manifesting, for example, in suppressed binding affinities orders of magnitude lower than those in solution[6,14,15,17,18].

A consequence of molecular crowding is that a DNA probe layer presents a high, ~0.1 mol $L^{-1}$ concentration of immobilized negative charge. This charge density erects an electrostatic barrier to entry of like-charged would-be hybridization partners from solution. In order for hybridization to proceed, this barrier needs to be screened through the addition of salt such that the solution number density of mobile ions becomes comparable to that of the surface-bound DNA charge[17]. While this electrostatic screening benefits hybridization, it also suppresses electrostatic interactions between the probe layer and the underlying support that could be used to control or to monitor the surface hybridization state. As an alternative approach that avoids this drawback, electrostatic hindrance to surface hybridization can be tempered through the use of neutral (i.e. uncharged) probes, such as peptide nucleic acids (PNAs)[19,20] and Morpholinos[21]. Moreover, because the probe layer starts from an uncharged state, binding of charged nucleic acid targets is expected to elicit stronger structural changes, thus enhancing prospects for analysis of the hybridization reaction through purely electrostatic means.

From the selection of neutral probes, the high binding affinity of PNAs provides strong mismatch discrimination[19,22] that is expected to be well suited to genotyping and to resequencing. Applications of PNAs have typically relied on 16 mer or shorter sequences[23-26] since longer strands, or ones containing long stretches of pyrimidines and purines, become increasingly challenging to prepare[27-29] and have greater potential for cross-reactivity with mismatched sequences. PNAs are thus expected to be less well suited to applications such as gene expression and pathogen detection which benefit from longer probe lengths, up to 70 nt,[30,31] to provide robust identification of a target's unique origin (i.e. a specific gene or biological entity). In such instances Morpholinos, which place few constraints on sequence design or length, are expected to be advantageous. Morpholinos also mitigate some of the difficult physicochemical properties of neutral DNA analogues; for example, they are about 100-fold more soluble than comparable PNAs and their relatively stiff backbone reduces propensity toward self-aggregation[32].

BRIEF SUMMARY OF THE INVENTION

One goal of the present invention is to present origins of electrostatic signatures of hybridization on charge-neutral Morpholino layers, and to contrast this behavior with that of DNA probe films. The preparation of thiolate-anchored Morpholino films on gold supports is described first, based on adaptation of "mixed monolayer" methods used for production of molecularly precise DNA films consisting of the probe plus an alkanethiol surface-blocking agent[33-36]. The efficacy of the blocking-agent to passivate against surface-adsorption of the probe backbone is critical, and was confirmed with infrared spectroscopy. Electrochemical methods were used to study hybridization between Morpholino probes and DNA targets. Changes in layer organization, from probe-target binding, were related to the layer's capacitive (charging) response. The sensitivity and direction of the response, including observation of contrast inversion, were controllable by the surface potential, $V_{DC}$, at which the response was sampled. At the molecular level these relationships can be explained from the combined influence of $V_{DC}$ and surface charge, stemming from hybridization of target strands, on the local populations of mobile ions, as further interpreted through Poisson-Boltzmann modeling. "Dual-color" redox labeling was used to simultaneously track surface populations of probe and target strands to derive a quantitative mapping between the capacitive response and the target occupancy. Viewed as a diagnostic tool for surface hybridization, these label-free capacitive measurements exhibit un-optimized sensitivities comparable to established methods such as surface plasmon resonance and quartz crystal microbalance techniques.

DETAILED DESCRIPTION OF PREFERRED EMBODIMENTS

Figure 1:
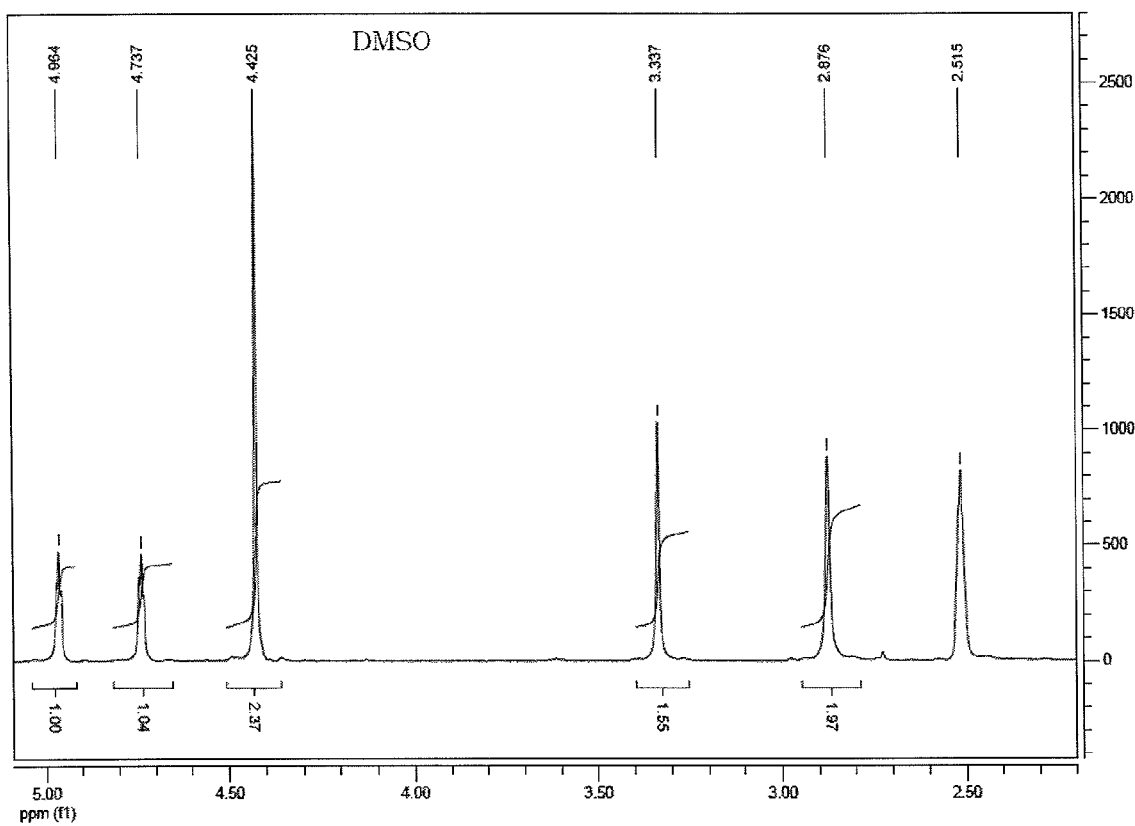
FIG. 1. 1H NMR spectrum of ferrocenecarboxylic acid-NHS ester product.

The general area of application of this invention is to enable identification of the base sequence of nucleic acid molecules in a sample ("targets" or "analytes") by surface hybridization (i.e. base-specific binding) to molecules ("probes") immobilized on a solid support. For example, this invention describes the capability to monitor the progress of the hybridization reaction using Morpholino-type probes and label-free, in-situ, real-time capacitive transduction. Illustrative areas of application are in monitoring of gene expression from biological cells, and in identification/quantification of pathogens (or other biological entities) based on presence of their genomic material.

Nucleic acid analysis by surface hybridization typically relies on DNA probes, with fluorescent methods used to detect binding of target nucleic acids. In these methods, targets need to be fluorescently labeled by one of numerous possible methods.[3] Label-free methods avoid the costs and experimental variability associated with the labeling protocols. The dominant label-free detection platforms are based on surface plasmon resonance[69] and quartz-crystal microbalance[72] methods. The present invention demonstrates that, by using uncharged Morpholino probes, hybridization of charged nucleic acid targets results in pronounced physicochemical changes at the surface which can be detected through changes in the surface capacitance. Capacitive detection has all the benefits of label-free methods (lower costs, less experimental variability, freedom from perturbation of the hybridization reaction due to presence of labels) and, in addition, is characterized by (1) sensitivities comparable to or exceeding those of surface plasmon resonance and quartz crystal microbalance methods, (2) significantly more modest requirements in terms of instrumental hardware, and (3) greater amenability to implementation in microelectronic (e.g. CMOS) biochip platforms.

In this invention, Morpholinos, a class of uncharged DNA analogues, are introduced for surface hybridization diagnostics based on capacitive transduction. Monolayers of Morpholino probes on gold supports can be fabricated with methods similar to those employed with DNA, and are shown to hybridize efficiently and sequence-specifically with target strands. Hybridization-induced changes in the interfacial charge organization can be analyzed with electrochemical methods to interpret and to quantify the extent of surface hybridization. Capacitive monitoring of the state of surface hybridization can yield both positive and negative contrasts (i.e. increases as well as decreases in surface capacitance), depending on surface populations of mobile ions as controlled by the read-out potential. Conditions of read-out potential for which capacitive detection produces optimal performance, as defined by highest sensitivity to coverage of bound target molecules and by independence of the capacitive signal on the read-out bias, are identified. Quantitative comparison of surface capacitance with target coverage (targets/area) reveals a near-linear relationship, and demonstrates sensitivities (limits of quantification based on a 10:1 signal-to-noise criterion) in the picogram per square millimeter range. Further improvements in sensitivity are expected at ionic strengths lower than the 0.2 mol per liter conditions explored thus far.

This invention is of general and broad interest to applications involving surface-based nucleic acid assays, defined as processes in which the sequence and/or amounts of nucleic acids in a sample are identified by base-specific binding on a solid support. Moreover, the invention is of interest to companies providing products for nucleic acid assays.

Materials and Methods.

Materials. Morpholino oligomers, purified by precipitation, were purchased from Gene Tools LLC. HPLC purified DNA probes and targets were purchased from MWG Biotech.

Table 1 lists the Morpholino and DNA sequences, their abbreviations, and experimental purpose used as illustrative examples.

yield was obtained. The FC1 product was an orange-yellow powder as described in reference 83. $^1$H NMR (300 MHz, DMSO, ppm): δ 2.515 (DMSO), 2.876 (s, 4H, —COCH$_2$—

TABLE 1

Morpholino and DNA sequences.

| Sequence | | Abbreviation |
|---|---|---|
| 5' NH$_2$-TTT TAA ATT CTG CAA GTG AT-CO(CH$_2$)$_3$SS(CH$_2$)$_3$CONH$_2$ 3'[A] Morpholino retinoblastoma RB1 marker probe; used for hybridization studies | (SEQ ID NO: 1) | PM1 |
| 5' NH$_2$-TTT TAA ATT CTG CAA GTG AT-(CH$_2$)$_3$SS(CH$_2$)$_3$OH 3' DNA probe; same sequence as PM1 | (SEQ ID NO: 1) | PD1 |
| 5' TTT TTT TCC TTC CTT TTT TT-CO(CH2)3SS(CH2)$_3$CONH$_2$ 3' [A] Morpholino probe; used for infrared reflection-absorption spectroscopy (IRRAS) studies | (SEQ ID NO: 2) | PM2 |
| 5' ATC ACT TGC AGA ATT TAA 3' DNA target; complementary to PM1 and PD1 | (SEQ ID NO: 3) | TD1 |
| 5' AAA AAA AGG AAG GAA AAA 3' DNA target; noncomplementary hybridization control | (SEQ ID NO: 4) | TD2 |

[A]The Morpholino PM1 and PM2 molecular structures are (m = 19):

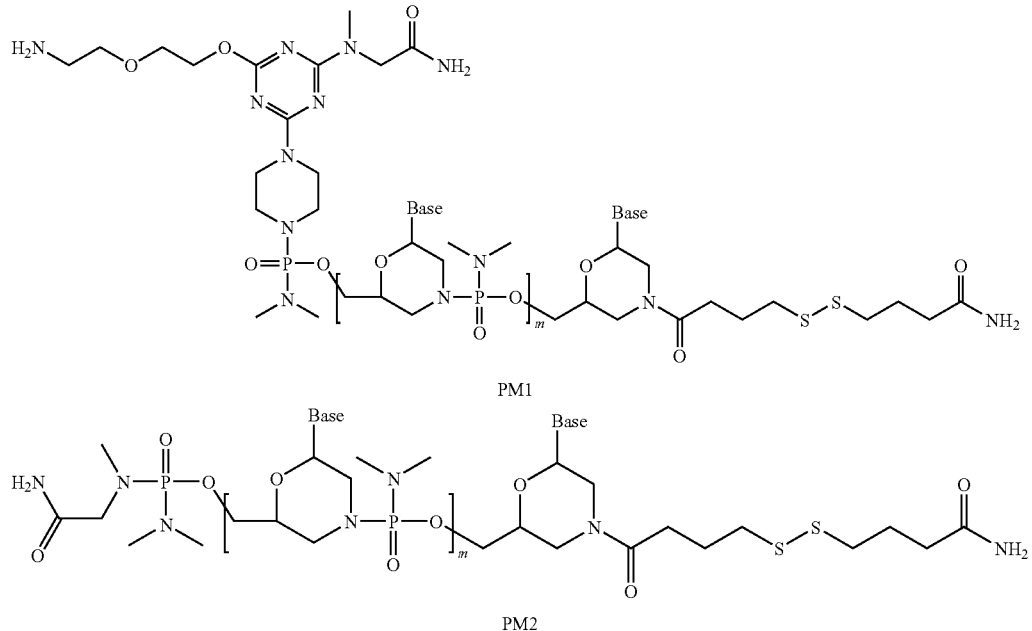

N-(2-ferrocene-ethyl) maleimide ("F2") was synthesized as described.[17] Synthesis of ferrocene monocarboxylic acid N-hydroxy succinimide ester ("FC1") was similar to published methods[37] and is detailed herein.

1. Synthesis of Ferrocenecarboxylic Acid-NHS Ester (FC1) Tag.

All reagents were obtained from Sigma-Aldrich and were used without purification. Molecular sieves were placed into tetrahydrofuran (THF) and methanol solvents to keep them free of moisture. The synthesis of FC1 followed closely the procedure reported by Takenaka and coworkers[81,82] with modifications as per references 83 and 84. The following reagents were combined and stirred for 1 hr at 0° C.: 0.26 g (1.1 mmol; FW: 230.05, 97% purity) of ferrocene carboxylic acid in 4.8 ml THF, 0.14 g (1.2 mmol; MW: 115.10) of N-hydroxysuccinimide (NHS) in 4.8 ml THF, and 0.25 g (1.2 mmol; MW: 206.33, 99% purity) of dicyclohexylcarbodiimide (DCC) in 2.4 ml THF. The mixture was then kept at 4° C. for 48 hr. The precipitate (dicyclohexylurea) was filtered off using a fritted funnel. The filtrate was evaporated to dryness and the obtained solid product (FC1) was washed with absolute methanol at 0° C on a fritted funnel. After drying a 70%

CH$_2$CO—), 3.337 (s, H$_2$O), 4.425 (s, 5H, Fc), 4.737 (t, 2H, Fc), 4.964 (t, 2H, Fc). FIG. 1 shows the corresponding spectrum.

2. Bioconjugation of Ferrocene Tags.

Electroactive tags F2 and FC1 were used to label target and probe molecules, respectively, to allow in-situ determination of strand surface coverage. Amine-terminated probes PM1 and PD1 were labeled with FC1 at the 5' end (FIG. 2) by combining 0.3 mmol L$^{-1}$ probe in 0.5 mol L$^{-1}$ pH 9.0 sodium carbonate buffer with a 150-fold excess of FC1, at room temperature for 16 hrs. Unreacted FC1 was removed on NAP-10 (GE Healthcare) and oligonucleotide purification cartridge (Applied Biosystems) prep columns, followed by reverse-phase HPLC (Beckman Coulter Gold® 125; Clarity 3 vm Oligo-RP column from Phenomenee). HPLC conditions for ferrocene modified DNA probes were 50° C., 0.5 ml min$^{-1}$, and a linear gradient of 12 to 60% methanol in hexafluoroisopropanol/triethylamine buffer (HFIP-TEA; 100 mmol L$^{-1}$ HFIP, 4.5 mmol L$^{-1}$ TEA, pH 8.0) spread over 22 min. HPLC purification of Morpholino-ferrocene conjugates proceeded identically but using a gradient of 12 to 100% methanol in HFIP-TEA over 20 min, followed by 5 min at 100% methanol. The dominant fraction of labeled material was collected, and a second run performed to confirm purity. Conjugates were dried in a vacuum centrifuge (Vacufuge®, Eppendorf) and stored dry at −14° C. until use. For experiments requiring labeled targets, additional TD1 and TD2 sequences (Table 1) were purchased that also included a 3' disulfide (—$(CH_2)_3SS(CH_2)_3OH$) end modification. Labeling of target oligonucleotides started with deprotection of the disulfide endgroup with dithiothreitol (DTT) to liberate the sulfhydryl moiety, in 10 mmol $L^{-1}$ DTT, 10 mmol $L^{-1}$ TRIS, 1 mmol $L^{-1}$ EDTA, pH 8.0, for 2 hrs. Excess DTT was removed on a NAP-10 column, followed by reacting the ~25 μmol $L^{-1}$ target solution with 30-fold excess of F2 (FIG. 2) in 150 mmol $L^{-1}$ pH 8.0 potassium phosphate buffer overnight. Final purification, collection, drying, and storage procedures were as for DNA probes.

3. Fitting of Cyclic Voltammetry Data.

The peak charges $Q_{F2}$ and $Q_{FC1}$ were determined by decomposing the experimentally measured current $I_{EX}$ into its three components $$I_{EX} = I_B + I_{T,F2} + I_{T,FC1} \tag{S1}$$

representing contributions from the baseline ($I_B$) and tag ($I_{T,F2}$; $I_{T,FC1}$) currents. The mathematical form of $I_B$ was established empirically using monolayers of unlabeled probes—i.e. in the absence of $I_{T,F2}$ and $I_{T,FC1}$—and was found to be well captured by a combination of linear and stretched exponential functions, $$I_B = a_1 + a_2 V + a_3 \exp(V^{a_4}/a_5) \tag{S2}$$

where V is the applied potential and $a_1$ through $a_5$ are adjustable parameters. The tag currents follow from theory[85], $$I_T = a_{6,T} \exp(a_{8,T}(V-a_{7,T}))/[1+\exp(a_{8,T}(V-a_{7,T}))]^2 \tag{S3}$$

where $a_{7,T}$ is the tag's formal potential at the surface and $a_{6,T}$ and $a_{8,T}$ are parameters related to the peak area and width.

Probe and target coverages were calculated from the forward half of cyclic voltammograms. An initial guess for the baseline slope $a_2$ and the intercept $a_1$ was obtained from a cyclic voltammogram before hybridization—with only the probe FC1 peak present—using data between 0.1 V and 0.2 V where the probe tags do not contribute. The parameters $a_1$ and $a_2$ were then fixed and used in a fit of the first cyclic voltammogram that included both target and probe peaks, covering data from 0.1 V and up to the positive potential limit (typically 0.65 V). This fit yielded the additional baseline parameters $a_3$, $a_4$ and $a_5$, which were then held fixed for all subsequent cyclic voltammograms that tracked the growth of the target peak. The remaining six parameters $a_{6,i}$, $a_{7,i}$ and $a_{8,i}$ (i=FC1, F2) were fit for each successive trace to minimize the root-mean-squared error between $I_{EX}$ and the calculated current $I_B + I_{T,F2} + I_{T,FC1}$ (equation S1). The reason for excluding the first 0.1 V from fitting is that the model is not designed to capture the initial charging transient that occurs at the onset of a CV measurement. The numerical routine was implemented in FORTRAN. An initial optimization was carried out using the Nelder-Mead downhill simplex algorithm, followed by quasi-Newton optimization to more quickly converge to the error minimum.

4. Preparation of Probe Monolayers.

Samples for electrochemical measurements were prepared on 1.6 mm diameter polycrystalline gold disk electrodes. The electrodes were first cleaned by mechanical polishing with 1 μm diamond suspension, rinsing with methanol and deionized (18.2 MΩ cm) water, and finally by potentiodynamic cycling in 0.5 mol $L^{-1}$ $H_2SO_4$ for 60 cycles from 0.24 V to 1.54 V (vs Ag/AgCl/3 mol $L^{-1}$ NaCl reference) at 0.1 V $s^{-1}$. The electrodes were again rinsed with deionized water and, without drying, the roughness factor r (r=actual area/geometric area) was determined from double layer capacitance.[38,39] Values of r ranged from 1.4 to 1.6. After a final rinse with deionized water, the still-wet electrodes were covered by probe deposition solution.

Probe solutions were pipetted directly onto cleaned supports. Probes were suspended at 0.25 μmol $L^{-1}$ probe in deionized water (Morpholino probes) or in 1 mol $L^{-1}$ $MgCl_2$ (DNA probes). Following immobilization of the probes, samples were rinsed with deionized water and then blocked in 1 mmol $L^{-1}$ mercaptopropanol (MCP; Sigma-Aldrich 95% purity) in water for 90 min for DNA layers, or for 150 min for Morpholino layers. The longer blocking times for Morpholinos improved reproducibility of baselines in cyclic voltammetry experiments. The samples were rinsed again, and placed into target-free hybridization buffer (see below). All transfer steps were accomplished wet to minimize chances for adsorption of atmospheric contaminants.

Samples for infrared reflection-absorption spectroscopy (IRRAS) were prepared on standard size, float glass microscope slides coated with 5 nm of titanium and 100 nm of gold (EMF Corp., Ithaca, N.Y.). The slides were cleaned for 10 min in 120° C. "piranha" solution consisting of 7:3 mixture of concentrated sulfuric acid and 30% hydrogen peroxide solution in water (CAUTION: piranha solution is highly oxidizing and must not be stored in tightly capped containers on account of gas evolution). Following a rinse with deionized water the still-wet slides were covered with probe deposition solution. Conditions were as for preparation of electrochemical samples except that, in addition, slides were prepared also without the final MCP blocking step. After drying with a nitrogen stream, samples were used immediately for 1 RRAS measurements.

5. IRRAS Measurements.

IRRAS spectroscopy was performed on a Perkin Elmer Spectrum 100 spectrometer equipped with an 80° specular reflectance accessory (PIKE Technologies). Spectra were collected from 900 $cm^{-1}$ to 4000 $cm^{-1}$ at 4 $cm^{-1}$ resolution, with software correction for presence of water vapor bands. Cleaned, but otherwise unmodified, gold-coated slides served as background.

6. Electrochemical Characterization.

Electrochemical measurements were performed on a CHI660C workstation (CH Instruments) with a three electrode cell comprised of the modified Au working electrode, a platinum wire counter electrode, and an Ag/AgCl/3 mol $L^{-1}$ NaCl reference electrode (Bioanalytical Systems; 0.209 V vs NHE at 25° C.). All potentials are reported relative to this reference. A glass sleeve salt bridge was used to guard against leakage of NaCl from the reference electrode's reservoir into the electrolyte. The electrolyte, which also served as the hybridization buffer, was 0.2 mol $L^{-1}$ pH 7.0 sodium phosphate buffer. A fixed target concentration of 25 nmol $L^{-1}$ and probe coverages of about $5\times10^{12}$ probes $cm^{-2}$ were used. When data were not being collected the electrochemical cell was kept off.

Figure 3:
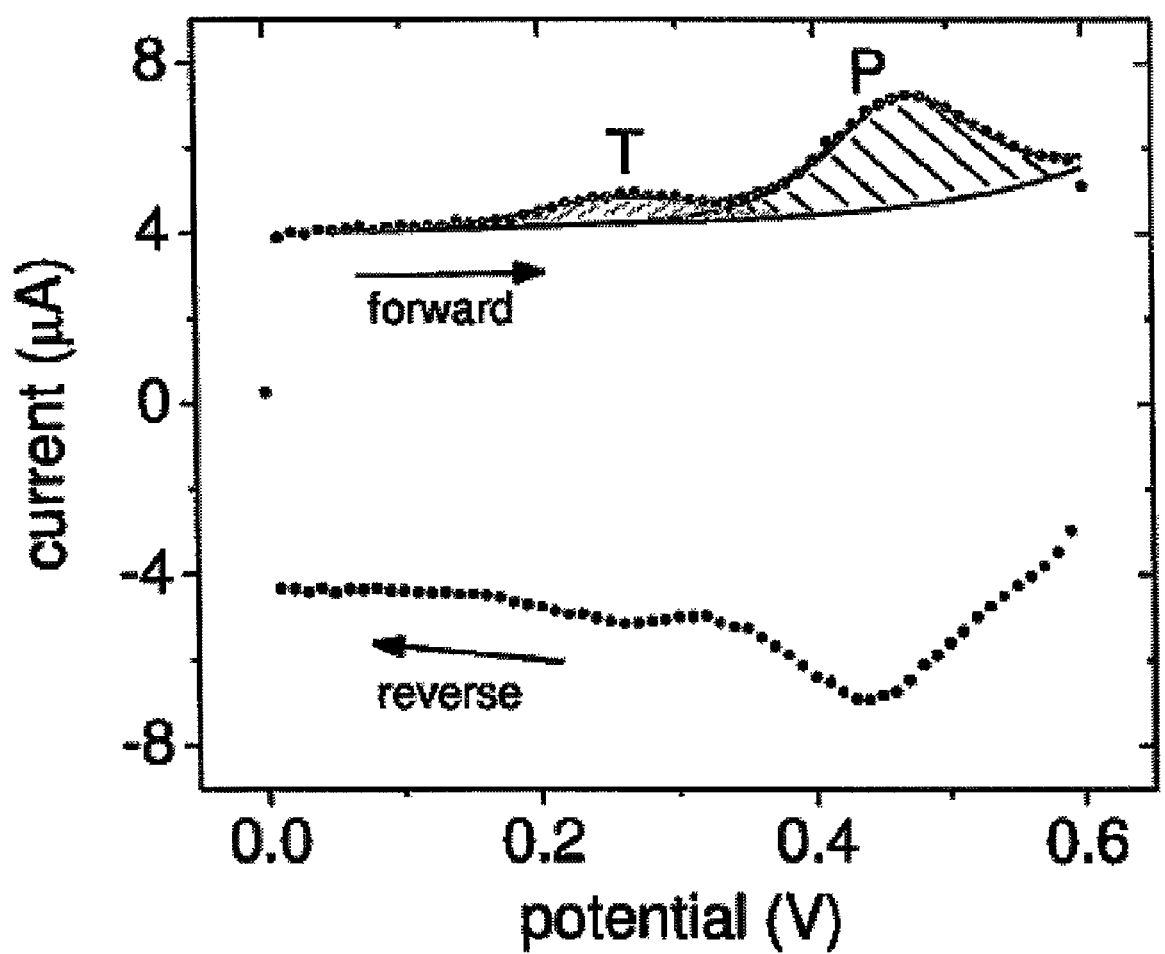
FIG. 3. Points (●): Experimental data. The CV scan starts from 0 V, moves along the forward trace to 0.6 V, and returns to 0 V along the reverse trace. The "T" and "P" peaks are from oxidation of target F2 and probe FC1 tags. The curves are computer-generated fits used to calculate $Q_{FC1}$ and $Q_{F2}$. Black line (-): baseline current $I_B$ (equation S2); green line (-): current $I_{T,F2}$ from target tags (equation S3); blue line (-): current $I_{T,FC1}$ from probe tags (equation S3); red line (-): total current $I_{tot}=I_B+I_{TF2}+I_{T,FC1}$.

Cyclic voltammetry (CV) measurements to determine the instantaneous coverage of ferrocene-labeled strands used a scan rate of 20 V $s^{-1}$ from 0 V to 0.6 V or to 0.65 V, requiring approximately 0.07 s per cycle. Probe and target surface coverages, $S_p$ and $S_T$, were calculated from the charge Q associated with oxidation of their ferrocene tags:

$$S_p = Q_{FC1}/(eA_g r) \quad S_T = Q_{F2}/(eA_g r) \tag{1}$$

where $e = 1.60 \times 10^{-19}$ C is the elementary charge, $A_g$ is the geometric area occupied by the probe layer, and r is the measured roughness factor. $Q_{FC1}$ and $Q_{F2}$ are total charges from the oxidation FC1→FC1$^+$+e$^-$ and F2→F2$^+$+e$^-$, respectively, corresponding to integration of the blue and green areas in FIG. 3 after converting the potential axis to time. Each probe and target possesses one ferrocene tag. The "T" peak near 0.25 V represents increased current due to oxidation of F2, and confirms presence of surface-bound target molecules. The probe FC1 signal, labeled "P", is observed near 0.45 V. On the reverse scan the tags are reset back to the neutral ferrocene state. The figure also shows fits to the data from which $Q_{FC1}$ and $Q_{F2}$ were determined. Fits were calculated by an automated computer routine described above.

In AC impedance (ACT) measurements, (1) a steady bias, $V_{DC}$, is imposed to set up the surface environment (e.g. distribution of mobile ions) and, (2) the charge-flow (current) response of this environment to perturbations in potential is sampled using a weak sinusoidal read-out function added to $V_{DC}$. Under the experimental conditions used, the response consisted only of charging currents, with the electrochemical cell behaving as a series combination of a resistance, R, representing the electrolyte, and a differential capacitance per area, $C_d$, representing the probe-modified working electrode. $C_d$ characterizes the surface organization of the probe layer and, for a series RC arrangement, is calculated from the measured out-of-phase impedance Z" using $|Z"|=1/(2\pi f \cdot A_{gr} C_d)$. f is the read-out frequency. Z" is related to experimental quantities using $Z"=-V_{ac} I_{op}(I_{ip}^2+I_{op}^2)$ with $V_{ac}$ the magnitude of the imposed read-out function, and $I_{ip}$ and $I_{op}$ the magnitudes of the measured in-phase and out-of-phase current components, respectively. A useful interpretation of $C_d$ is as a metric of the near-surface screening of electric fields: more effective screening correlates with higher capacitance because greater charge dob must be placed on the electrode to achieve a potential increment dV (see equation 2 below). Screening can be provided by polarization of the surface environment, as governed by the local dielectric properties, and/or by redistribution of mobile ionic charge.

An ACI measurement consisted of stepping the surface bias $V_{DC}$ from 0.25 V to −0.2 V in 0.025 V steps, and back, with $C_d$ determined at each step. A full $C_d$-loop took 1 min, and was performed once every 5 mm during the course of hybridization. A read-out frequency f=5435 Hz and ac potential magnitude of 5 mV rms were used. This frequency corresponded to a phase angle of 45° to 50°, and was sufficiently low to avoid secondary capacitive charging observed in the presence of the salt bridge at high frequencies, yet high enough to minimize contributions from spurious interfacial charge transfer that become more prominent at low frequencies.

7. Theoretical Calculation of $C_d$.

Theoretical predictions of the behavior of $C_d$ were used to guide interpretation of observed experimental trends. $C_d$ is defined by the derivative of the surface charge per area of the electrode, eo, with respect to the electrode potential V $$C_d = \frac{d\sigma_0}{dV} \quad (2)$$

$$\sigma_0 = -\varepsilon\varepsilon_0 \frac{dV}{dx}\bigg|_{0+\leftarrow x} \quad (3)$$

where equation 3 follows from Gauss' Law. Here $\epsilon$ is the material dielectric constant (relative static permittivity), so is the permittivity of vacuum and x is the perpendicular distance from the electrode surface. V(x) was calculated by numerical integration of the Poisson-Boltzmann equation, $$\frac{d^2 V}{dx^2} = -\frac{\rho(x)}{\varepsilon(x)\varepsilon_0} \quad (4)$$

$$\rho(x) = z_1 e c_1(x) + \sum_i z_j e c_{j\infty} \exp(-z_j eV(x)/kT)\exp(-\beta_j(x)) \quad (5)$$

$\rho(x)$ is the concentration of charge at x, e is the unit charge (1.60×10$^{-19}$ C), $z_I$ and $c_I$ are the valence and concentration of immobile charged sites (e.g. $c_I$ might represent concentration of DNA backbone phosphate residues), T is absolute temperature, k is the Boltzmann constant, and $z_j$, $c_{j\infty}$, and $\beta_j$ are the valence, solution concentration, and partitioning penalty of species j, where j ranges over all ions free to partition between solution and the probe layer. For example, if in the probe layer $\beta_{Na+}=1$, then there is a 1 kT penalty to transport a Na$^+$ cation from solution to the layer (e.g. from changes in solvation interactions) in addition to the eV term.

Equations 4 and 5 were solved for V(x) by modeling the MCP/probe film/electrolyte structure as a multilayer inside of which each layer k, of width $t_k$, was specified by constant values of $\epsilon_k$, $c_{Ik}$, and $\beta_k$. Runge-Kutta-Verner fifth and sixth order methods were used to integrate equation 4, expressed as two ordinary differential equations $dy_1/dx=-\rho k/(\epsilon_k\epsilon_0)$ and $dy_2/dx=y_1$, where $y_2=V(x)$. The integration was performed from the probe layer/electrolyte interface at $x_B=\Sigma_k t_k$ to the electrode surface at x=0, with continuity of the potential V(x) and electric displacement $\epsilon dV/dx$ at boundaries between layers. The two required initial conditions were (1) a specified value for $V(x_B)$ and (2) the corresponding potential gradient dV/dx at $x=x_B$. The gradient can be calculated by integrating equation 4 analytically once; if $x_1$ and $x_2$ are two positions within layer k, then $$\frac{dV}{dx}\bigg|_{x2} = \left(\left(\frac{dV}{dx}\right)_{x1}^2 - \frac{2eN_A}{\varepsilon_k\varepsilon_0}\bigg[z_{Ik}c_{Ik}(V_2-V_1) + \frac{kT}{e}\sum_j c_j\exp(-z_jeV_2/kT-\beta_{jk})\{\exp(z_je(V_2-V_1)/kT-1\}\bigg]\right)^{1/2} \quad (6)$$

For the semi-infinite electrolyte with $x_2=x_B$, $x_1=\infty$, Chd I=0, and $\beta_j=0$, and with dV/dx and V going to 0 as x→∞, equation 6 simplifies to $$\frac{dV}{dx}\bigg|_{x_B} = \left(-\frac{2kTN_A}{\varepsilon\varepsilon_0}\sum_j c_j\{1-\exp(-z_jeV(x_B)/kT)\}\right)^{1/2} \quad (7)$$

which served as the second initial condition. $C_d$ was obtained from the calculated V(x) by numerical differentiation, according to equations 2 and 3.

The electrolyte was modeled as containing sodium cations and three types of phosphate anions with relative concentrations governed by acid-base equilibria: $H_2PO_4^-$, $HPO_4^{2-}$, and $PO_4^{3-}$. For the experimental 0.2 mol L$^{-1}$ pH 7.0 phosphate buffer, the concentrations used are 0.315 mol L$^{-1}$ Na$^+$, 0.0846 L$^{-1}$ mol $H_2PO_4^-$, 0.115 mol L$^{-1}$ $HPO_4^{2-}$, and 5.54×10$^{-7}$ mol L$^{-1}$ $PO_4^{3-}$. The electrolyte dielectric constant was taken to be 80, and the temperature was 295° K.

Results and Discussion.

1. IRRAS Studies of MCP Passivation.

Direct contact of probes with the solid support can be detrimental to hybridization activity; for example, singlestranded DNA probes are known to adsorb to gold through base-surface interactions[40,41] that result in surface-bound conformations with poor hybridization activity.[11,33,36] Hybridization activity can be restored by treatment, or passivation, of the surface with alkanethiols such as mercaptohexanol or mercaptopropanol (MCP) with a hydrophilic surface chemistry to which the probes do not strongly adsorb. These displacer molecules assemble into a monolayer coating that lifts the probe backbone off the support, leaving the strands attached through their thiolate bond only, in an end-tethered geometry favorable to hybridization.

Morpholino probes, through their bases, were similarly expected to exhibit an affinity for gold, motivating examination of whether MCP is able to successfully displace these interactions. The thymine-rich probe PM2 was selected for these experiments because thymine-gold interactions yield an IR. marker band in the region 1580 to 1600 $cm^{-1}$ [42,43], attributed to C=O stretches of chemisorbed thymine.[42] A successful passivation of the surface with MCP, in which the probe backbone is displaced from direct contact with the support, should be accompanied by a disappearance of this marker band.

Figure 4:
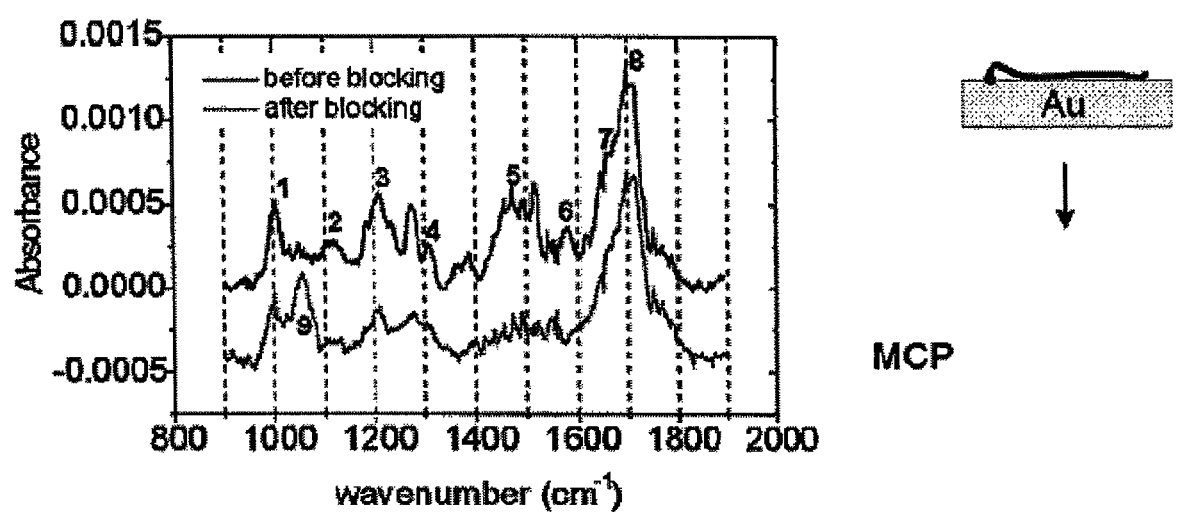
FIG. 4. IRRAS spectra before (black -) and after (gray -) blocking of a PM2 monolayer with mercaptopropanol (MCP). Assignments for numbered peaks are provided in Table 2. Peak 6 is diagnostic of contact between thymine bases and the Au support.

FIG. 4 compares IRRAS spectra of a PM2 monolayer before and after MCP blocking. The assignments for the dominant spectral bands are given in Table 2. The disappearance of the marker band, corresponding to peak 6, after MCP passivation indicates that displacement of adsorptive contacts between thymine bases and the support was successful. In parallel, the appearance of the C—OH stretch at 1060 $cm^{-1}$ (peak 9) confirms the surface presence of MCP.

TABLE 2

IRRAS spectral assignments for Morpholino monolayers.

Figure 2:
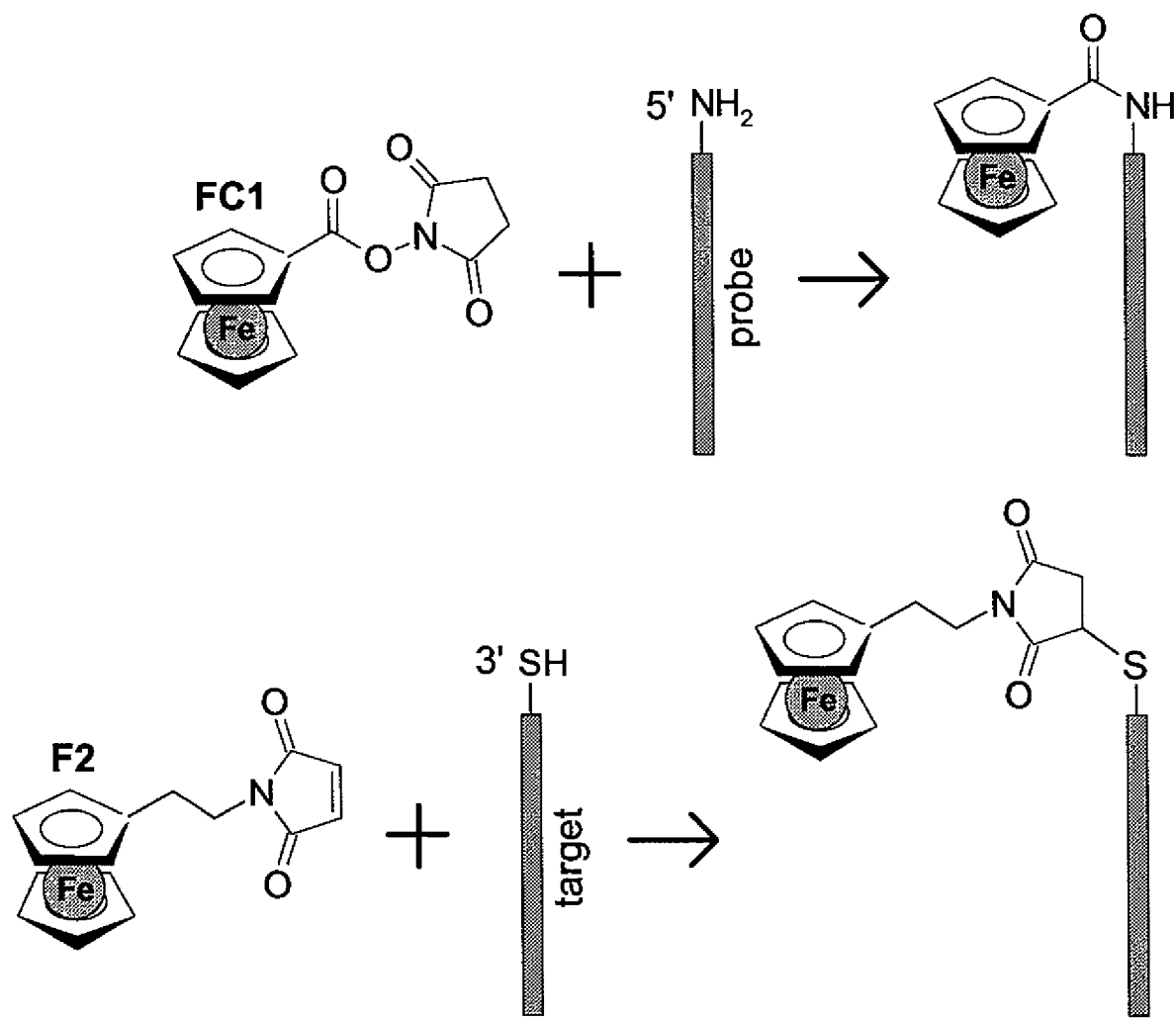
FIG. 2. Top: Probe molecules were labeled with the electroactive tag FC1 using NHS ester to amine conjugation. Bottom: Target molecules were labeled with F2 via thiol-maleimide coupling.

| Peak # FIG. 2 | Position ($cm^{-1}$) | Primary Attribution | Reference |
|---|---|---|---|
| 1 | 1000 | P—O—C asymmetric stretch | 44 |
| 2 | 1120 | C—O—C asymmetric stretch | 44 |
| 3 | 1210 | P=O stretch | 44 |
| 4 | 1310 | Phosphoroamidate $(CH_3)_2N$—P vibration | 45 |
| 5 | 1420-1520 | Various bands (thymine, phosphoroamidate | 42, 45 |
| 6 | 1580 | C=O stretch of chemisorbed thymine | 42 |
| 7 | 1670 | C4=O stretch of thymine | 42 |
| 8 | 1705 | C2=O stretch of thymine | 42 |
| 9 | 1060 | C—OH stretch of mercaptopropanol | 44 |

2. Charge Organization of Hybridized Morpholino Monolayers.

A specific state of surface hybridization defines a unique combination of immobilized and mobile ion concentrations at the surface. Conversely, the response of this environment to an applied potential can be used to characterize the state of hybridization and in principle provides for a convenient, label-free approach to diagnostics. However, significant challenges arise in quantitatively relating a label-free electrochemical response (e.g. surface capacitance, surface potential, field-effect transduction) with molecular coverage of analyte. The underlying relationships between surface organization and the measured response are obscure and at times counter-intuitive; for example, both decreases[46-50] and increases[51-53] in surface capacitance due to hybridization have been reported, illustrating that even the direction of change can be unpredictable. Similarly, orders of magnitude disparities exist in estimated sensitivities of field-effect transduction, despite similar mechanisms of contrast[54].

Figure 5:
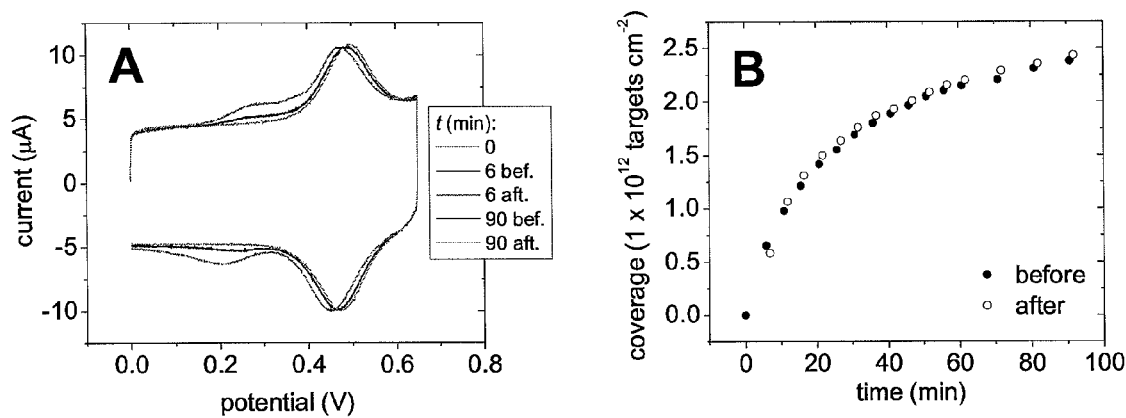
FIG. 5. The impact of variation in surface potential $V_{DC}$ on extent of hybridization during $C_d$ measurement. Probe coverage: $7.0 \times 10^{12}$ probes $cm^{-2}$. Buffer: 0.2 M pH 7.0 sodium phosphate. (A) Sample CV traces. The t=0 trace (green line) was taken immediately prior to addition of target, and shows only the Morpholino probe peak at 0.48 V. After 6 minutes of hybridization the "6 bef." voltammogram (black line) was measured, then an ac impedance $C_d$ loop requiring 55 s to complete was carried out between −0.2 and 0.05 V with 0.025 V steps, followed by measurement of the "6 aft." voltammogram (red trace). A target peak starts to appear at around 0.25 V. A pair of "before" and "after" voltammograms is also shown after 90 minutes of hybridization. CV settings: 20 V s$^{-1}$ between 0 and 0.65 V. (B) Corresponding target coverages determined by integration of target peaks from forward (anodic) half waves, from CVs determined immediately before (filled points) or after (hollow points) a $C_d$ loop.

In this section, the aim is to fundamentally understand the physical changes induced in charge organization of Morpholino films undergoing hybridization, and to compare these to when DNA probes are used. Optimization of Morpholino. assays, which perform best at low salt concentrations where DNA probes do not function, will be reported separately. At the buffer strength (0.2 mol $L^{-1}$ pH 7.0 sodium phosphate) used for the present experiments both probe types hybridize well. In the experiments that will be described, the surface state was characterized at a point in time during the course of hybridization as a function of applied surface potential, $V_{DC}$, through the change in surface capacitance, $\Delta C_d$ ($V_{DC}$), brought on by probe-target binding. In turn, $\Delta C_d$ can be interpreted in terms of the near-surface ionic concentrations and dielectric strength. All of the experiments of this section used unlabeled targets in order to extend the positive limit on $V_{DC}$ up to 0.25 V without interference from tag electroactivity in the determination of $C_d$, at the cost of foregoing quantification of target coverage (quantitative comparison of target coverage with $\Delta C_d$ is postponed to section 3). The control experiments disclosed below showed that (1) target coverage was not significantly perturbed by changes in surface potential during $C_d$ measurements (Impact of Changes in Potential on Target Coverage) and (2) hybridization of Morpholino films with sequence-specific, with binding of non-complementary TD2 targets below detection (Nonspecific Binding of Targets to Probes: CV Measurements).

a. Impact of Changes in Potential on Target Coverage (FIG. 5)

Measurement of a $C_d$-$V_{DC}$ loop required 1 min to complete, during which time the surface bias was perturbed away from the hybridization potential of 0 V. Since changes in surface bias may be expected to have an impact on the extent of hybridization, there was concern that different parts of a $C_d$-$V_{DC}$ loop could correspond to significantly different coverages of target molecules. This issue was addressed by performing hybridization controls with F2-labeled targets, using a sample with probe coverage of $7.0 \times 10^{12}$ probes $cm^{-2}$ and under 0.2 M pH 7.0 sodium phosphate buffer. Control experiments consisted of performing a CV measurement immediately before and after each $C_d$-$V_{DC}$ loop to determine the pre- and post-execution target coverages. To minimize degradation of target F2 tags via the oxidized ferricinium form[86,87], what would compromise accurate determination of coverage, $V_{DC}$ was constrained to lie below the onset of F2 oxidation; i.e. not to exceed 0.05 V (note: all potentials are referenced to Ag/AgCl/3M NaCl). Thus, in the control experiments potential was looped between −0.2 V and 0.05 V, compared to between −0.2 V and 0.25 V for full $C_d$ scans that used unlabeled targets.

FIG. 5A plots CV traces measured just before introduction of target at t=0, and immediately before and after a $C_d$ loop at t=6 min and also at t=90 min. In FIG. 5B, the target coverages determined from all the CV curves are plotted against time, both for measurements performed immediately before (filled points) and after (hollow points) a $C_d$ loop. Changes in hybridization during execution of a $C_d$ loop were modest; i.e. nearly the same extent of hybridization (within 10%) was sampled by all points along a $C_d$-$V_{DC}$ trace. In FIG. 5B a systematic, if slight, increase in target coverage is apparent for values determined from "after" CVs. While this increase may be a real effect, given the small differences it could also be an artifact brought on, for example, by variations in the CV baseline due to structural perturbation of the probe layer from stepping of the surface potential (during the $C_d$ measurement). Such changes could subtly, and systematically, influence the CV fitting algorithm.

b. Nonspecific Binding of Targets to Probes: CV Measurements (FIG. 6)

CV hybridization series, testing for sequence-nonspecific adsorption of TD2 targets to Morpholino PM1 probes, were carried out at conditions of $4.0 \times 10^{12}$ probes $cm^{-2}$ and 0.2 M pH 7.0 sodium phosphate buffer. To provide a stricter test of nonspecific adsorption, a surface potential of 0.1 V, instead of 0 V, was used to facilitate adsorption of the negatively charged, noncomplementary TD2 targets. CV scans were obtained every 5 minutes at 20 V $s^{-1}$.

Figure 6:
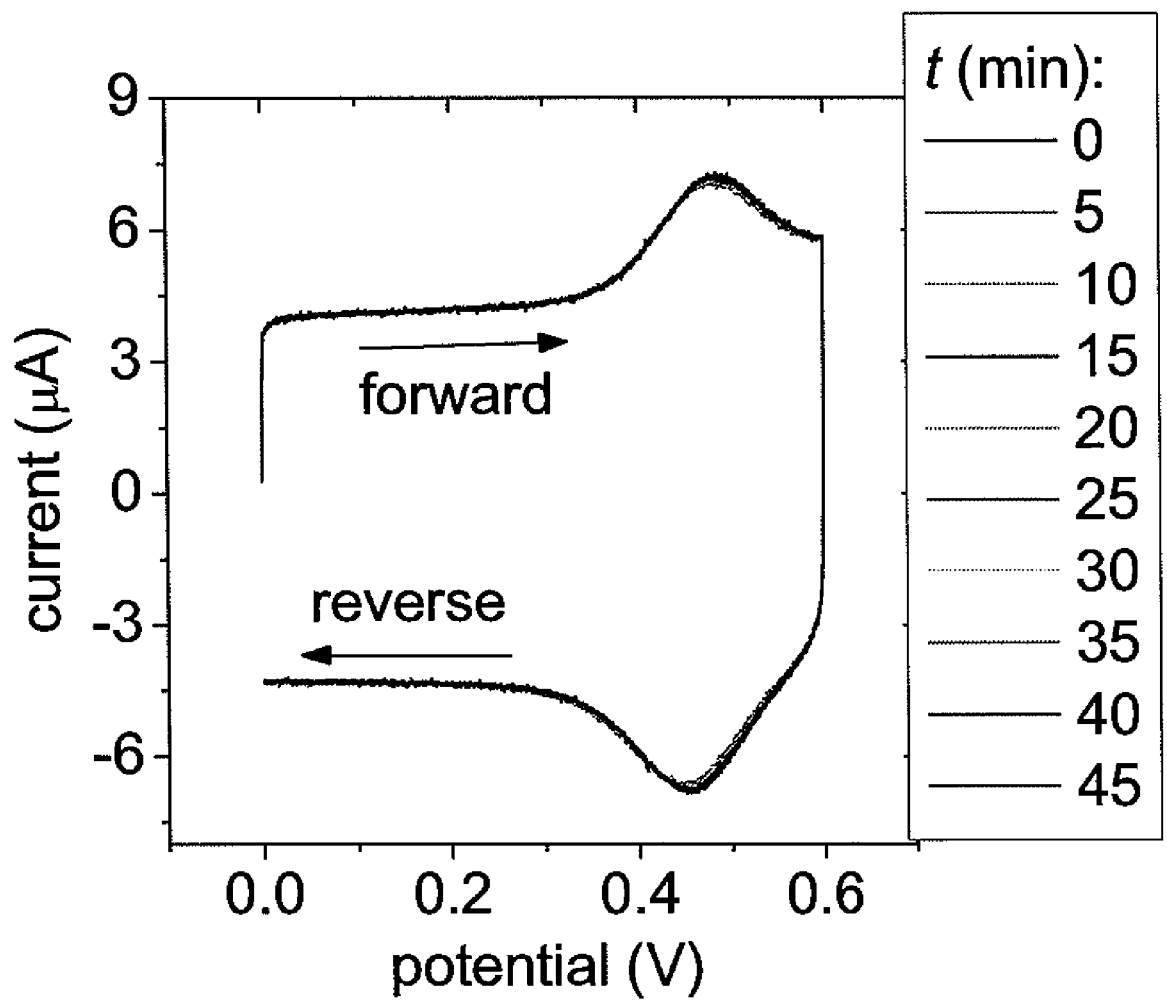
FIG. 6. Ten consecutive CV voltammograms, measured over 45 minutes, in the presence of 25 nM of F2-labeled TD2 target. Conditions: $4.0 \times 10^{12}$ probes cm$^{-2}$, 0.2 M pH 7.0 sodium phosphate, 0.1 V surface bias.

FIG. 6 plots ten consecutive scans measured over 45 minutes in the presence of 25 nM, F2-labeled TD2. A probe peak near 0.48 V is from the probes' FC1 tag. Presence of adsorbed targets would be signified by an F2 peak close to 0.25 V. The lack of F2 electroactivity indicates that noncomplementary binding was below the detection limit of $\sim 1 \times 10^{11}$ targets $cm^{-2}$. The low nonspecific adsorption was further confirmed by lack of response to addition of TD2 targets during label-free assays, as described herein.

Figure 7:
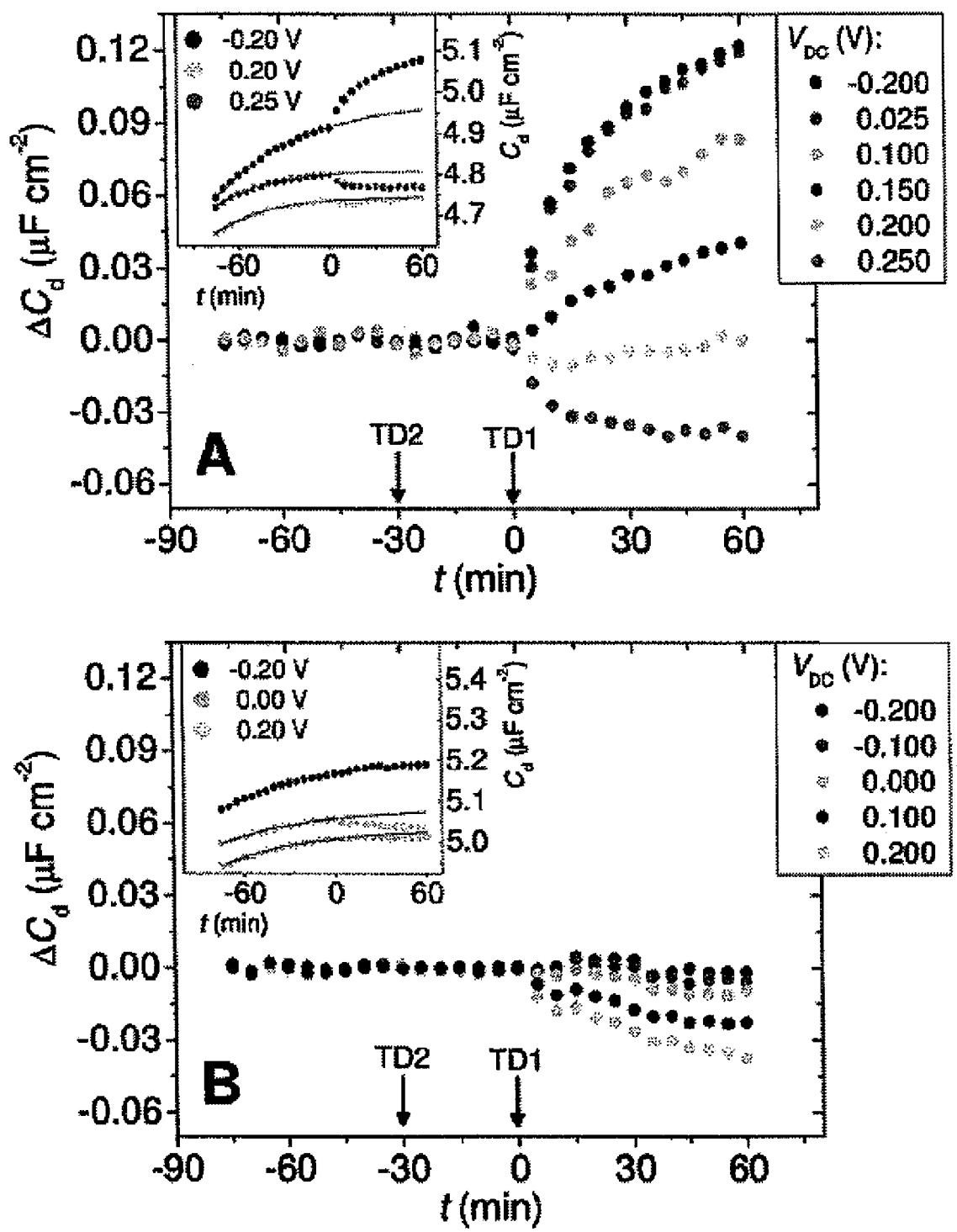
FIG. 7. (A) Main panel: Change in capacitance $\Delta C_d$ for Morpholino layers undergoing hybridization as a function of measurement bias $V_{DC}$. Arrows indicate addition of non-complementary TD2 and complementary TD1 targets. Inset: Examples of raw $C_d$ vs time data (points) and fitted baselines $f_B$ (red solid lines), at three settings of $V_{DC}$. $\Delta C_d$ was calculated as the difference between $C_d$ and the baseline. Conditions: $4.9 \times 10^{12}$ probes cm$^{-2}$, 25 nmol L$^{-1}$ target, pH 7.0 0.2 mol L$^{-1}$ sodium phosphate buffer. (B) Same as (A) but for DNA probe layers at $5.1 \times 10^{12}$ probes cm$^{-2}$ and otherwise identical conditions.

FIG. 7 compares the evolution of $\Delta C_d$ for Morpholino (FIG. 7A) and DNA (FIG. 7B) probe films in the presence of target molecules. The insets show raw data in the form of traces of $C_d$ vs time. Prior to addition of complementary target TD1 at time t=0, only a featureless increase in the baseline, on the order of 1% per hour, was observed in the raw data. The source of this increase is not known with certainty but is suspected to reflect gradual loss of MCP. Empirically, the shape of the baseline could be represented by a first order process; that is, the baseline function $f_B$ was modeled as $f_B = A_1 - A_2 \exp(-A_3 t)$, with $A_1$, $A_2$, and $A_3$ determined from a least squares fit to data prior to hybridization, $-75$ min<t<0 min (see insets to FIGS. 7A and 7B). $\Delta C_d$, attributed to binding of target molecules, follows from $\Delta C_d = C_d - f_B$. For each run, probe layers were first measured under target-free buffer, next under 25 nmol $L^{-1}$ non-complementary TD2 target for 30 min ($-30$ min<t<0 min), and finally under a TD1:TD2 mixture with each target present at 25 nmol $L^{-1}$. Addition of non-complementary TD2 at t=$-30$ min did not produce a resolved response at any of the potentials, whereas addition of the complementary TD1 target at t=0 mm immediately led to a change in $\Delta C_d$.

Strikingly, as shown in the main panel of FIG. 7A, the response for Morpholino films to hybridization was tunable, with a change in sign (contrast inversion) from positive to negative as $V_{DC}$ increased past 0.2 V. Moreover, in the range from $-0.2$ V to 0.025 V the response was nearly independent of $V_{DC}$, making this range attractive for diagnostic applications. Above 0.025 V, $\Delta C_d$ started to decrease with $V_{DC}$ and became negative beyond the contrast inversion point at 0.2 V. In comparison, hybridization of DNA targets to DNA probes produced $\Delta C_d$ 0 when measured at negative biases, below $-0.1$ V. As $V_{DC}$ increased, contrast improved and an increasingly negative ($\Delta C_d < 0$) response to hybridization was observed.

Figure 8:
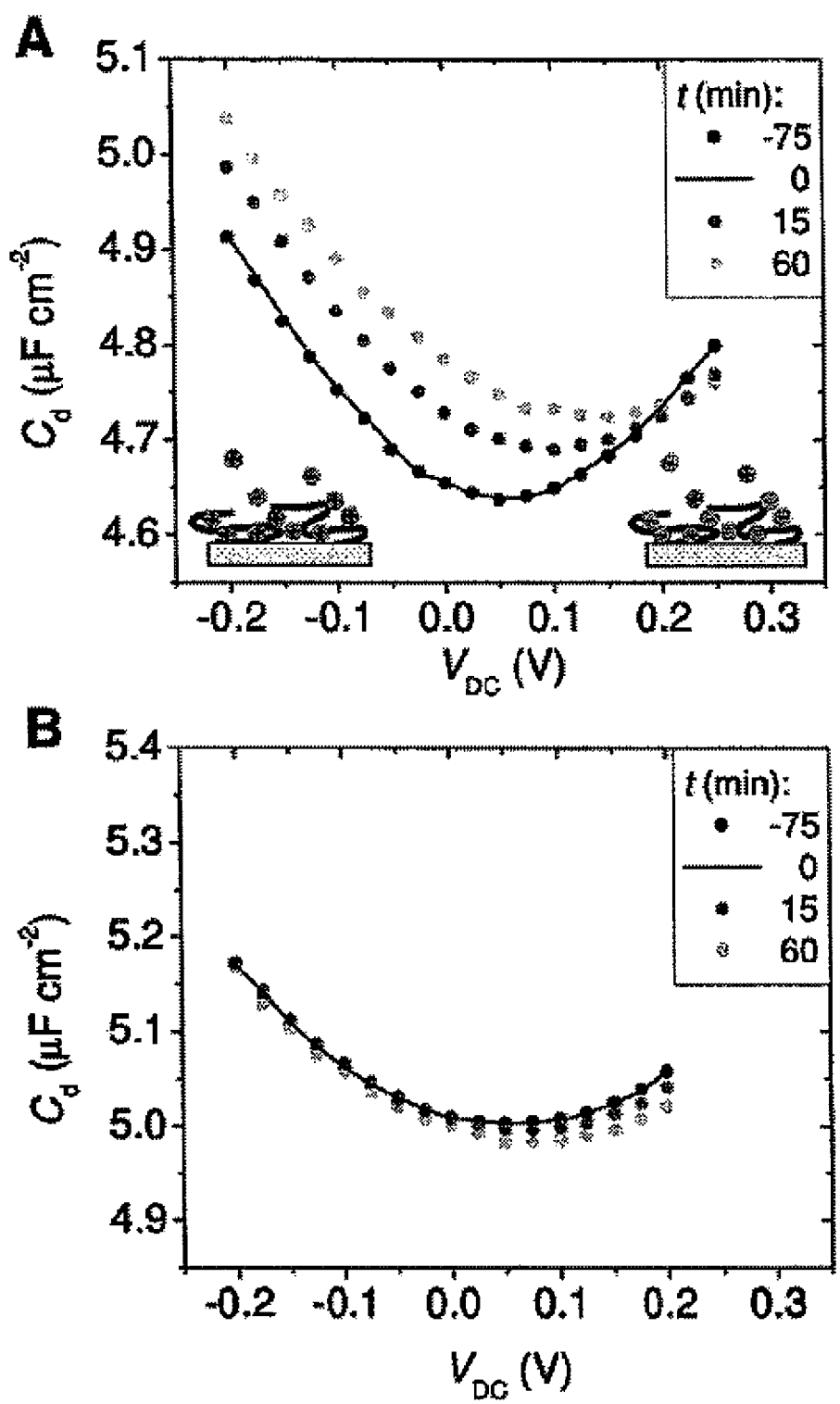
FIG. 8. $C_d$ ($V_{DC}$) traces as a function of time for (A) Morpholino and (B) DNA probe films. t=0 (black line) corresponds to introduction of complementary TD1 target and onset of hybridization. Shift in $C_d$ due to baseline drift was corrected relative to t=0 by plotting $C_d(t) = C_{d,raw}(t) - (f_B(t) - f_B(0))$, where $f_B(t) - f_B(0)$ is the change in baseline between t and 0 min, and $C_{d,raw}(t)$ is the unprocessed data.

The data in FIG. 7 show that, depending on $V_{DC}$ and probe type, binding of target molecules can manifest as an increase, a decrease, or a null response. Understanding the origins of this diversity of trends provides insight into the physical changes that accompany surface hybridization. In FIG. 8, the data are replotted to show the full dependence of $C_d$ on $V_{DC}$ at selected time points, for Morpholino (FIG. 8A) and DNA (FIG. 8B) probe layers. Between t=$-75$ mm (black points) and t=0 min (black trace) the probe films were kept under buffer and non-complementary TD2 target, with little if any change taking place. Introduction of complementary TD1 target at t=0 produced horizontal and vertical displacements of the $C_d(V_{DC})$ trace. As illustrated by the cartoons in FIG. 8A, the ubiquitous increase in $C_d$ at the extremes of $V_{DC}$ is attributed to potential-driven accumulation of solution ions near the surface: phosphate anions at more positive potentials and sodium cations when $V_{DC}$ is swept negatively. The elevation in surface concentration of mobile ions provides for more efficient ionic screening, and hence higher capacitance.[55]

The displacements of the $C_d(V_{DC})$ traces in FIG. 8 were interpreted with the help of the Poisson-Boltzmann (PB) model, described by equations 2 through 7. The MCP layer was modeled using a width $t_{MCP}$=0.67 nm[56], a dielectric constant $\epsilon_{MCP}$=4.4, and β=1000 for all solution ions. These settings reproduced the experimental capacitance of about 5.6 μF $cm^{-2}$ for a pure MCP monolayer. Setting the partitioning penalty β to 1000 effectively renders the MCP layer impermeable to ions. The description of the Morphoino layer proved more complex. One expectation is that unhybridized probes are in a collapsed, desolvated state. The principal reason for this suspicion is that the surface concentration of $\sim 0.1$ to 1 mol $L^{-1}$ significantly exceeds the bulk solubility of $\sim 1$ mmol $L^{-1}$ [57], implying that the probes exist as a precipitated film. As a first approximation, therefore, the layer thickness tp was set to the collapsed "dry" value of 0.52 nm, derived from the measured probe coverage and a volume of 0.53 $nm^3$ per nucleotide.[58]

Figure 9:
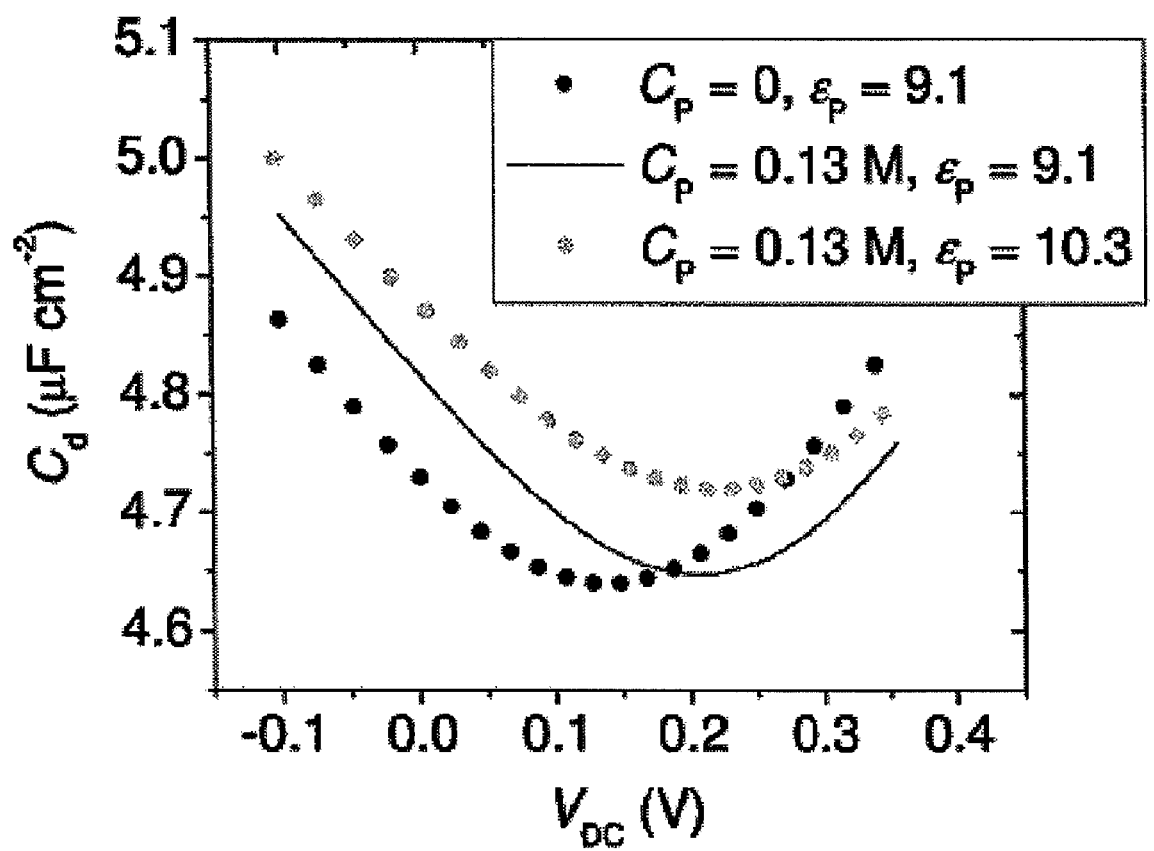
FIG. 9. PB theory calculations, illustrating the effect of (1) an increase in immobilized negative charge $C_p$ of the probe layer from 0 (black points) to 0.13 mol L$^{-1}$ (blue line), and (2) an increase in dielectric constant $\epsilon_p$ of the probe layer from 9.1 (blue line) to 10.3 (green points). The shape of the curve traced out by the black points corresponds, approximately, to t=0 data in FIG. 7A, while the green trace can be compared to the t=60 min data. MCP layer parameters: $t_{MCP}$=0.67 nm, $\epsilon_{MCP}$=4.4, $\beta_{j,MCP}$=1000 for all ions. Morpholino probe layer parameters: $t_{MCP}$=0.52 nm, $\beta_{Na+,P}$=0, $\beta_{H_2PO_4^-,P}$=1.8, $\beta_{PHPO_4^{2-},P}$=1000, $\beta_{PO_4^{3-},P}$=1000. Electrolyte parameters: T=295° K, 0.2 mol L$^{-1}$ pH=7.0 phosphate buffer.

In order to capture the experimental upturn in $C_d$ at positive and negative biases (FIG. 8A), it was necessary to allow sodium $Na^+$ and monovalent phosphate $H_2PO_4^-$ ions to partition into the probe film under the influence of $V_{DC}$. This condition was met by keeping the partitioning penalty β small for these ions (FIG. 9 caption). However, partitioning of divalent phosphate ($HPO_4^{2-}$) led to an overly exaggerated upturn at positive $V_{DC}$; thus, only monovalent phosphate was assumed to penetrate.[59] Finally, it is important to note that experiments express $V_{DC}$ relative to a reference electrode, with an unknown absolute potential, whereas calculations express $V_{DC}$ relative to solution. This leads to an offset in $V_{DC}$ between calculated and experimental curves.[60]

FIG. 9 shows that two simple adjustments in model parameters were able to qualitatively reproduce experimentally observed changes in $C_d$ due to hybridization. The first type of adjustment consists of addition of immobile charge sites to the Morpholino layer ($c_I$ term in equation 5), the predominant outcome of which is a horizontal shift of the $C_d(V_{DC})$ curve parallel to the potential axis. In FIG. 9 this is illustrated by the black and green traces representing, respectively, a neutral film and a layer with 0.13 mol $L^{-1}$ concentration of immobile negative charge.[61] The horizontal shift arises because of an altered permselectivity of the film. The effect can be recast in hybridization terms as follows. Binding of targets introduces immobile, negatively charged sites to the probe layer. The presence of these sites depletes anions and accumulates cations in the film, and alters the value of $C_d$. In order to restore $C_d$ and the cation-to-anion balance at the surface to their pre-hybridization values, a more positive $V_{DC}$ must be applied to compensate for the effect of the negatively charged sites. This positive offset in $V_{DC}$ manifests as a translation of the entire $C_d(V_{DC})$ curve toward positive potentials.

The above explanation and the PB model present a simplified description in that the charge of hybridized targets was assumed to be strictly immobile. This approximation is partly justified by the observation that, at the high frequency (5435 Hz) used for measurement, surface-tethered DNA oligonucleotide chains do not respond significantly to oscillating surface fields[62]; thus, the main contribution to $C_d$ is expected to be from movement of small ions whose mobility is not impaired by backbone connectivity, or the large mass-to-charge ratio of DNA.

The second type of adjustment illustrated in FIG. 9 is a change in the dielectric constant profile. In general, such a change could result from variation in composition, thickness, homogeneity, or other structural rearrangement of the probe layer brought on by hybridization. The local dielectric constant represents capacity of the surface environment to screen electric fields through polarization: higher values correspond to more effective screening, allowing greater surface charge to build up in response to an increment in potential, and increasing $C_d$ (equation 2). A change in dielectric constant thus raises or lowers $C_d$,[63] causing a vertical displacement of the $C_d$ ($V_{DC}$) curve. This is illustrated in FIG. 9, where an upward displacement was produced by increasing the dielectric constant of the probe film from 9.1 (blue curve) to 10.3 (green trace).

For Morpholino films, the impact of hybridization on the $C_d(V_{DC})$ curve can be summarized as a rightward and an upward translation (FIG. 8A). The rightward displacement signifies a change in permselectivity that favors cations and expels anions; as discussed above, this outcome is expected from hybridization of negatively charged targets. The upward displacement indicates improved dielectric screening. These dielectric changes are expected to reflect various effects, difficult if not impossible to disentangle. For example, hybridization may improve solvent compatibility of the probe layer, elevating the local dielectric constant through increased water content, and concomitantly leave a thinner underlayer of unhybridized, collapsed probes on the surface. It is the cumulative effect of such changes that would be reflected in the observed, upward displacement in $C_d$.

Hybridization to DNA probes resulted in a rightward displacement of the $C_d(V_{DC})$ curve (FIG. 8B) indicating that in this case, also, binding of target molecules shifted the cation: anion balance in favor of cations. The qualitative impact of hybridization on permselectivity was therefore same for Morpholino as for DNA probe layers. However, in contrast to the Morpholino results, the $C_d(V_{DC})$ curve shifted slightly downward. Decrease in capacitance for hybridized DNA probe films was previously attributed to lowering of polarization screening because of volumetric displacement of solvent molecules by DNA targets,[46-48] whose dielectric constant is lower. This explanation also agrees with the present observations. Compared to Morpholino films, target hybridization to a DNA probe layer should have little impact on the layer's solvent compatibility because of the good solubility of DNA probes.

The origins of the contrast inversion reported in FIG. 7A for Morpholino hybridization are now clear. When $\Delta C_d$ is measured at a $V_{DC}$ negative of the $C_d$ minimum, the unhybridized and uncharged layer is initiated in a cation-rich state. In this scenario, subsequent binding of target strands is accompanied by additional accumulation of cations, rather than expulsion of anions of which there are very few in proximity of the surface. The extra cations are needed to ensure electroneutrality. In this cascade of events, hybridization elevates the local concentration of small ions, ionic screening is enhanced, and thus $C_d$ increases—leading to positive contrast ($\Delta C_d > 0$). However, as shown by data positive of $V_{DC}=0.2$ V in FIG. 8A, contrast can be also negative ($\Delta C_d < 0$). Since the $C_d(V_{DC})$ curve is also translated upward, the decrease in $C_d$ cannot be attributed to a lowering of the dielectric constant (e.g. from displacement of water molecules by targets). Rather, the explanation is sought in a lowering of the local ionic strength. A diminished ionic strength would imply that hybridization of targets causes a drop in concentration of mobile ions at the surface. This outcome is expected if, as targets bind, electroneutrality is satisfied by expulsion of anions from the surface. Indeed, at sufficiently positive biases the surface concentration of anions will greatly exceed that of cations, making anion-expulsion the default mechanism used to satisfy electroneutrality; i.e. the surface ionic strength will drop as targets bind, leading to a negative contrast. The target countercharge, in this case, must then be mostly provided by positive charge on the electrode.

3. Mapping $\Delta C_d$ to Target Coverage.

The experiments in FIGS. 7 and 8 helped elucidate physical mechanisms of surface hybridization on Morpholino monolayers, but did not provide quantitative dependence of $\Delta C_d$ on the extent of hybridization. This dependence was explored in a separate series of measurements using F2-labeled targets, probe coverage of $5.8 \times 10^{12}$ probes cm$^{-2}$, and six $V_{DC}$ settings: 0, −0.01, −0.02, −0.03, −0.04, and −0.05 V. These potentials fall within the diagnostically optimal window in which contrast was strongest and largely potential-independent (FIG. 8A). $C_d$ was determined every 5 minutes at all six potentials and, immediately following, probe coverage $S_P$ and target coverage $S_T$ were measured using cyclic voltammetry (CV). The combined $C_d$ and CV measurement required 30 s to complete. After subtraction of the $f_B$ baseline, the six $\Delta C_d$ values from each time point were averaged and standard deviations were calculated. Target and probe coverages were expressed as the hybridization conversion x, defined by $x=S_T/S_P$.

Figure 10:
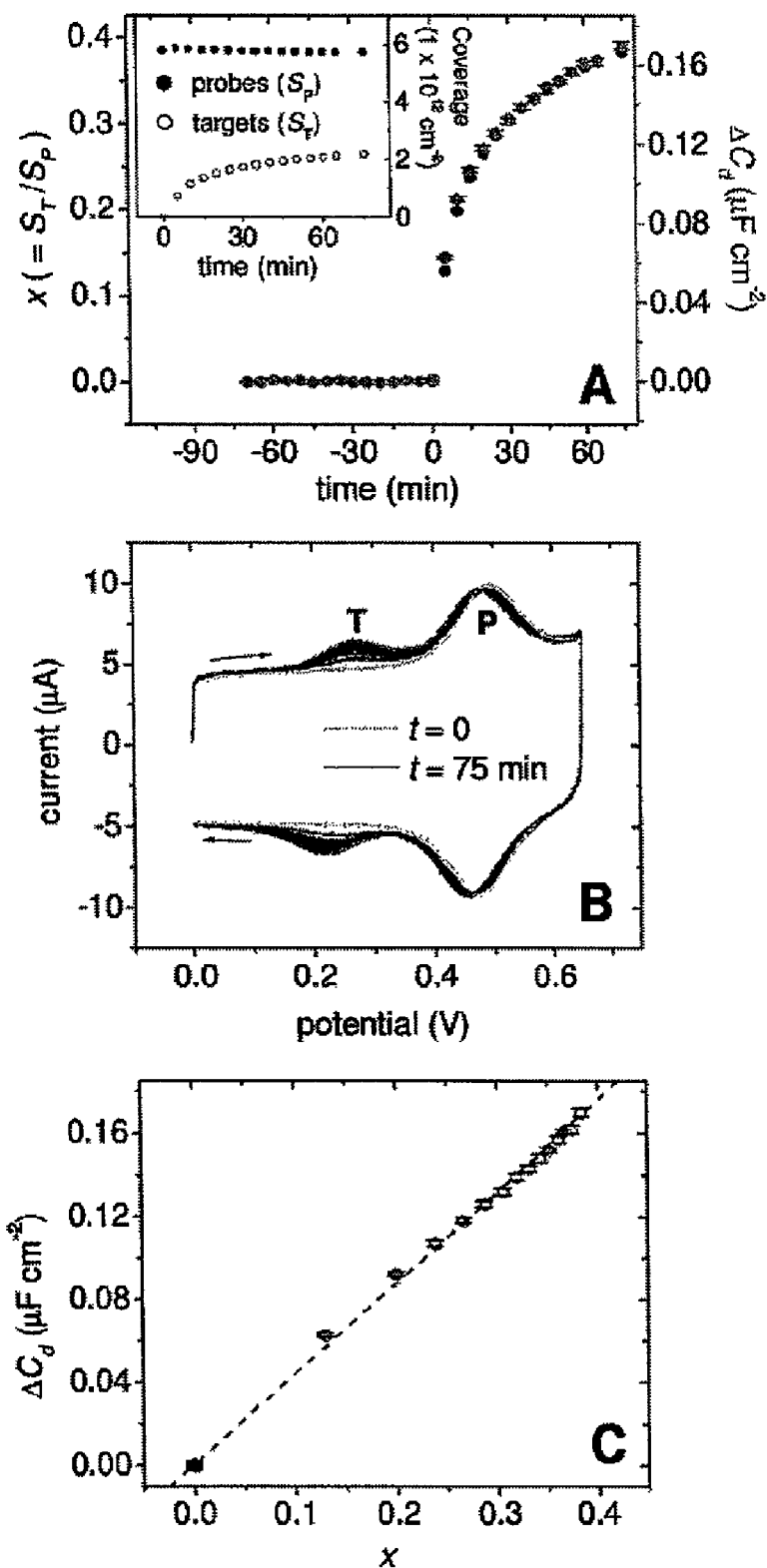
FIG. 10. (A) Main panel: Time traces of surface conversion $x = S_T/S_P$ (black points) and of $\Delta C_d$ signal (red points) for hybridization of TD1 targets to PM1 probes. Plotted $\Delta C_d$ values are averages of measurements at $V_{DC}$ of 0, −0.01, −0.02, −0.03, −0.04, and −0.05 V. Error bars give the standard deviations. Buffer: 0.2 mol L$^{-1}$ pH 7.0 sodium phosphate. Inset: Probe (filled points) and target (open points) coverages determined from cyclic voltammetry. (B) Cyclic voltammograms used for calculation of probe and target coverages. First (t=0) and last (t=75 mm) scans are highlighted in green and red, respectively. "T" marks the target peak, "P" marks the probe peak. (C) Dependence of $\Delta C_d$ on x. Dashed line: least-squares linear fit ($R^2$=0.9992).
Figure 11:
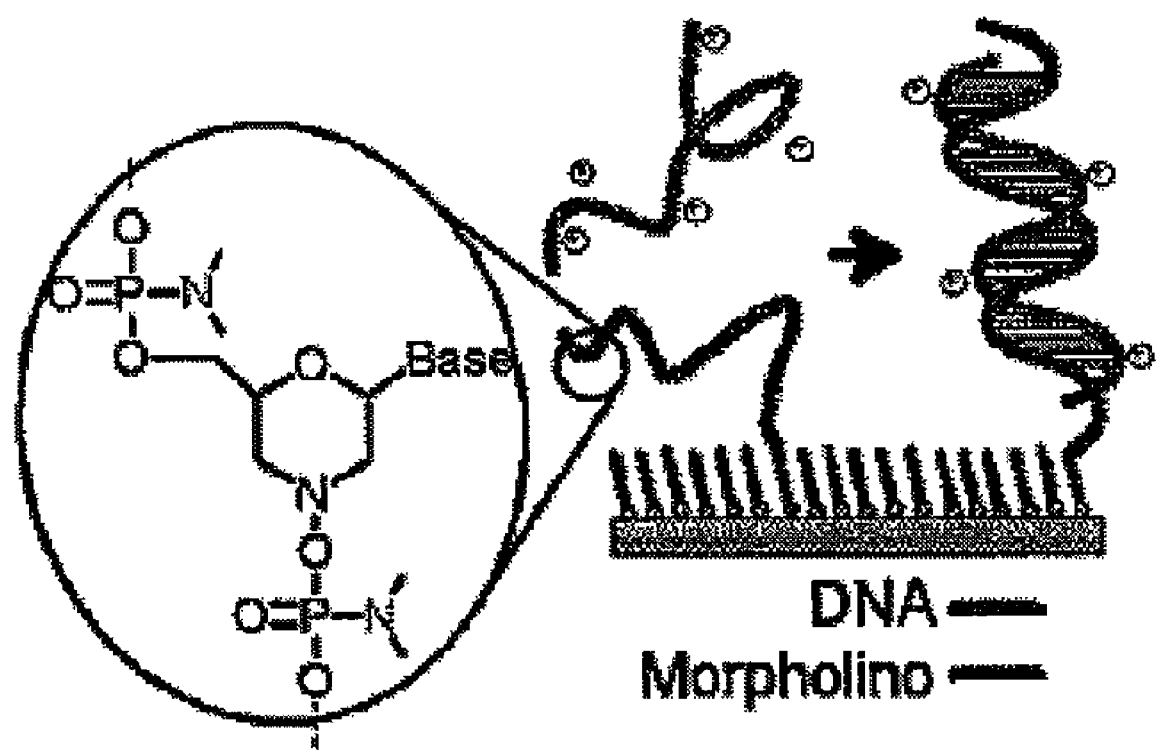
FIG. 11 is an illustration of hybridization between nucleic acids present in solution and Morphoino strands immobilized on a solid support, as described in this invention.

FIG. 10A plots x (black points) and $\Delta C_d$ (red points; error bars are standard deviations) as a function of time, with $t=0$ corresponding to addition of complementary TD1 target. The inset shows target and probe coverages calculated from the CV scans shown in FIG. 10B. The ~2% decrease in probe coverage is attributed in part to gradual tag degradation via the ferricinium state.[64,65] In FIG. 10B, the peak near 0.24 V is from targets while that near 0.48 V is from the probes. Surface, as opposed to solution, origins of the target signal were confirmed by noting that the peak current, measured from the baseline, scaled linearly with scan rate $dV/dt$.[66] During hybridization the probe CV peak shifted negatively by about −20 mV and slightly broadened (cf. green and red CV traces in FIG. 10B). This shift reflects the creation of a membrane potential[67,68] at the surface from the binding of negatively-charged targets, which facilitates oxidation of ferrocene by stabilizing the positively charged ferricinium state. FIG. 10C shows that $\Delta C_d$ and x were strongly correlated, with a near-linear relationship between the two quantities.

The label-free limit of quantification, $I_Q$, is defined as ten times $S_B$ where $S_B$ is the standard deviation of the background prior to hybridization (i.e. for −70<t<0). Performing this calculation on the data in FIG. 10A yields $s_B = 2.2 \times 10^{-10}$ F cm$^{-2}$ and $I_Q = 10 s_B = 2.2 \times 10^{-9}$ F cm$^{-2}$. The capacitance units can be converted to more informative units of target coverage by multiplying $I_Q$ by $dS_T/d\Delta C_d$, where $dS_T/d\Delta C_d = 1.3 \times 10^{19}$ targets F$^{-1}$ follows from $dS_T/d\Delta C_d = S_P (d\Delta C_d/dx)^{-1}$, and the slope $d\Delta C_d/dx$ of the line in FIG. 10C. This yields $I_Q = 2.9 \times 10^{10}$ targets cm$^{-2}$, representing 0.5% hybridization of the probe layer, or about 2.5 pg mm$^{-2}$ of target. This limit is comparable to or exceeds that of surface plasmon resonance and quartz crystal microbalance techniques[69-72], two popular methods for label-free monitoring of surface bioaffinity reactions.

Conclusions

Morpholino monolayers on gold can be prepared through direct adaptation of known chemistries for DNA monolayers, in which a thiolate bond serves to anchor Morpholino strands through one terminus to the surface, and the rest of the surface is passivated against nonspecific adsorption with a short chain alkanethiol. Hybridization of Morpholino monolayers, which are uncharged, with charged nucleic acid targets alters the dielectric and ionic strength characteristics of the surface environment. Hybridization of target molecules adds negative charge to the probe layer which has to be compensated by changes in local concentrations of small ions; i.e. by accumulation of cations and/or by expulsion of anions. Which adjustment mechanism dominates is tunable by the applied surface potential; e.g. at negative biases, when surface concentration of anions is small, accumulation of cations is the primary response mechanism. At positive potentials, expulsion of anions is dominant. These signatures of hybridization can be monitored through the surface differential capacitance $C_d$, where they lead to increases or decreases in $C_d$ depending on the relative surface populations of cations and anions. Similar phenomena would be expected to arise in electrostatic monitoring of surface hybridization using other uncharged probe molecules, such as PNAs[73-75] or nylon nucleotides.[76,77] The described physical processes are also analogous to those in other systems driven by charge effects; e.g. in metal-oxide-semiconductor structures, where semiconductor dopant sites take the place of immobile target charges and the phenomena of charge carrier inversion and accumulation correspond to accumulation of anions or cations in the probe layer.

A central motivation for the present study of Morpholino surface hybridization is prospects of label-free DNA or RNA analysis. Based on a 10:1 signal-to-noise criterion, $C_d$ measurements demonstrated limits of quantification down to $3 \times 10^{10}$ targets $cm^{-2}$, corresponding to several pg of material per $mm^2$. This performance matches that of other label-free methods, including surface plasmon resonance[69] and quartz crystal microbalance[72] techniques, that could be used for analysis of nucleic acids by surface hybridization. In the case of capacitive transduction, sensitivity is expected to improve at lower ionic strengths, under conditions more dilute than the 0.2 mol $L^{-1}$ phosphate buffer used. These and related performance issues will be analyzed separately. If label-free capacitive diagnostics are found promising, they can be adopted to microelectronic biochip platforms, in the spirit of recent efforts to develop fully-integrated chip hardware for label-based electrochemical nucleic acid assays.[47,78-80]

The foregoing detailed description of the preferred embodiments, the appendices, and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

REFERENCES (1) Denhardt, D. T., *Biochem. Biophys. Res. Commun.* 1966, 23, 641-646.

(2) Gillespie, D.; Spiegelman, S., *J. Mol. Biol.* 1965, 12, 829-842.

(3) Muller, H.-J.; Roder, T., Microarrays; Elsevier Academic Press: Burlington, Ma., 2006.

(4) Watterson, J. H.; Piunno, P. A. E.; Wust, C. C.; Krull, U., *J. Langmuir* 2000, 16, 4984-4992.

(5) Peterlinz, K. A.; Georgiadis, R. M.; Herne, T. M.; Tarlov, M. J., *J. Am. Chem. Soc.* 1997, 119, 3401-3402.

(6) Peterson, A. W.; Wolf, L. K.; Georgiadis, R. M., *J. Am. Chem. Soc.* 2002, 124, 14601-14607.

(7) Glazer, M.; Fidanza, J. A.; McGall, G. H.; Trulson, M. O.; Forman, J. E.; Suseno, A.; Frank, C. W., *Anal. Biochem.* 2006, 358, 225-238.

(8) Yao, D. F.; Kim, J.; Yu, F.; Nielsen, P. E.; Sinner, E. K.; Knoll, W., *Biophys. J.* 2005, 88, 2745-2751.

(9) Shchepinov, M. S.; Case-Green, S. C.; Southern, E. M., *Nucleic Acids. Res.* 1997, 25, 1155-1161.

(10) Wong, E. L. S.; Chow, E.; Gooding, J., *J. Langmuir* 2005, 21, 6957-15965.

(11) Gong, P.; Lee, C.-Y.; Gamble, L. J.; Castner, D. G.; Grainger, D. W., *Anal. Chem.* 2006, 78, 3326-3334.

(12) Gong, P.; Harbers, G. M.; Grainger, D. W., *Anal. Chem.* 2006, 78, 2342-2351.

(13) Henry, M. R.; Stevens, P. W.; Sun, J.; Kelso, D. M., *Anal. Biochem.* 1999, 276, 204-214.

(14) Nelson, B. P.; Grimsrud, T. E.; Liles, M. R.; Goodman, R. M.; Corn, R. M., *Anal. Chem.* 2001, 73, 1-7.

(15) Okahata, Y.; Kawase, M.; Niikura, K.; Ohtake, F.; Furusawa, H.; Ebara, Y., *Anal. Chem.* 1998, 70, 1288-1296.

(16) Ricci, F.; Lai, R. Y.; Heeger, A. J.; Plaxco, K. W.; Sumner, J., *J. Langmuir* 2007, 23, 6827-6834.

(17) Gong, P.; Levicky, R., *Proc. Natl. Acad. Sci. USA* 2008, 105, 5301-5306.

(18) Levicky, R.; Horgan, A., *Trends Biotechnol.* 2005, 23, 143-149.

(19) Egholm, M.; Buchardt, O.; Christensen, L.; Behrens, C.; Freler, S. M.; Driver, D. A.; Berg, R. H.; Kim, S. K.; Norden, B.; Nielsen, P. E., *Nature* 1993, 365, 566-568.

(20) Tomac, S.; Sarkar, S.; Ratilainen, T.; Wittung, P.; Nielsen, P. E.; Norden, B.; Graslund, A., *J. Am. Chem. Soc.* 1996, 118, 5544-5552.

(21) Summerton, J., In *Discoveries in Antisense Nucleic Acids (Advances in Applied Biotechnology)*; Brakel, C., Ed.; Portfolio Publishing Co.: The Woodlands, Tex., 1989, p 71-80.

(22) Ratilainen, T.; Holmn, A.; Tuite, E.; Nielsen, P. E.; Nordn, B., *Biochemistry* 2000, 39, 7781-7791.

(23) Germini, A.; Mezzelani, A.; Lesignoli, F.; Corradini, R.; Marchelli, R.; Bordoni, R.; Consolandi, C.; De Bellis, G., *J. Agric. Food Chem.* 2004, 52, 4535-4540.

(24) Weiler, J.; Gausepohl, H.; Hauser, N.; Jensen, O. N.; Hoheisel, J. D., *Nucleic Acids. Res.* 1997, 25, 2792-2799.

(25) Demidov, V. V.; Frank-Kamenetskii, M. D., *Trends Biochem. Sci.* 2004, 29, 62-71.

(26) Brandt, O.; Feldner, J.; Stephan, A.; Schroder, M.; Schnolzer, M.; Arlinghaus, H. F.; Hoheisel, J. D.; Jacob, A., *Nucleic Acids Res.* 2003, 31, e 119.

(27) Altenbrunn, F.; Seitz, O., *Org. Biomol. Chem.* 2008, 6, 2493-2498.

(28) Bergmann, F.; Bannwarth, W.; Tam, S., *Tetrahedron Lett.* 1995, 36, 6823-6826.

(29) Gildea, B. D.; Casey, S.; MacNeill, J.; Perry-O'Keefe, H.; Sorensen, D.; Coull, J. M., *Tetrahedron Lett.* 1998, 39, 7255-7258.

(30) Hughes, T. R.; Mao, M.; Jones, A. R.; Burchard, J.; Marton, M. J.; Shannon, K. W.; Lefkowitz, S. M.; Ziman, M.; Schelter, J. M.; Meyer, M. R.; Kobayashi, S.; Davis, C.; Dai, H.; He, Y. D.; Stephaniants, S. B.; Cavet, G.; Walker, W. L.; West, A.; Coffey, E.; Shoemaker, D. D.; Stoughton, R.; Blanchard, A. P.; Friend, S. H.; Linsley, P. S., *Nat Biotechnol.* 2001, 19, 342-347.

(31) Bodrossy, L.; Sessitsch, A., *Curr. Opin. Microbiol.* 2004, 7, 245-254.

(32) Summerton, J. E., *Lett. Pept. Sci.* 2004, 10, 215-236.

(33) Herne, T. M.; Tarlov, M. J., *J. Am. Chem. Soc.* 1997, 119, 8916-8920.

(34) Dandy, D. S.; Wu, P.; Grainger, D. W., *Proc. Natl. Acad. Sci. USA* 2007, 104, 8223-8228.

(35) Baker, B. R.; Lai, R. Y.; Wood, M. S.; Doctor, E. H.; Heeger, A. J.; Plaxco, K. W., *J. Am. Chem. Soc.* 2006, 128, 3138-3139.

(36) Levicky, R.; Herne, T. M.; Tarlov, M. J.; Satija, S. K., *J. Am. Chem. Soc.* 1998, 120, 9787-9792.

(37) Takenaka, S.; Uto, Y.; Kondo, H.; Ihara, T.; Takagi, M., *Anal. Biochem.* 1994, 218, 436-443.

(38) Oesch, U.; Janata, J. *Electrochim. Acta* 1983, 28, 1237-1246.

(39) Shen, G.; Tercero, N.; Gaspar, M. A.; Varughese, B.; Shepard, K.; Levicky, R., *J. Am. Chem. Soc.* 2006, 128, 8427-8433.

(40) Kimura-Suda, H.; Petrovykh, D. Y.; Tarlov, M. J.; Whitman, L. J., *J. Am. Chem. Soc.* 2003, 125, 9014-9015.

(41) Wolf, L. K.; Gao, Y.; Georgiadis, R. M., *Langmuir* 2004, 20, 3357-3361.

(42) Haiss, W.; Roelfs, B.; Port, S. N.; Bunge, E.; Baumgartel, H.; Nichols, R. J., *J. Electroanal. Chem.* 1998, 454, 107-113.

(43) Petrovykh, D. Y.; Kimura-Suda, H.; Whitman, L. J.; Tarlov, M. J., *J. Am. Chem. Soc.* 2003, 125, 5219-5226.

(44) Socrates, G., *Infrared Characteristic Group Frequencies*; 2nd ed.; John Wiley & Sons Inc.: New York, 1994.

(45) Harvey, R. B.; Mayhood, J. E., *Can. J. Chem.* 1955, 33, 1552-1565.

(46) Berggren, C.; Stalhandske, P.; Brundell, J.; Johansson, G., *Electroanalysis* 1999, 11, 156-160.

(47) Stagni, C.; Guiducci, C.; Benini, L.; Ricco, B.; Carrara, S.; Samori, B.; Paulus, C.; Schienle, M.; Augustyniak, M.; Thewes, R., *IEEE J. Solid-State Circuits* 2006, 41, 2956-2964.

(48) Shin, J. K.; Kim, D. S.; Park, H. J.; Lim, G., *Electroanalysis* 2004, 16, 1912-1918.

(49) Berggren, C.; Bjarnason, B.; Johansson, G., *Electroanalysis* 2001, 13, 173-180.

(50) Guiducci, C.; Stagni, C.; Fischetti, A.; Mastromatteo, U.; Benini, L.; Ricco, B., *IEEE Sensors J.* 2006, 6, 1084-1093.

(51) Mearns, F. J.; Wong, E. L. S.; Short, K.; Hibbert, D. B.; Gooding, J., *J. Electroanalysis* 2006, 18, 1971-1981.

(52) Yang, W. S.; Butler, J. E.; Russell, J. N.; Hamers, R. J., *Langmuir* 2004, 20, 6778-6784.

(53) Kafka, J.; Panke, O.; Abendroth, B.; Lisdat, F., *Electrochim. Acta* 2008, 53, 7467-7474.

(54) Poghossian, A.; Cherstvy, A.; Ingerbrandt, S.; Offenhausser, A.; Schoning, M. J., *Sens. Actuators, B* 2005, 111-112, 470-480.

(55) Backbone charges on DNA strands can also contribute to ionic screening; however, this contribution is expected to be relatively minor due to constraints imposed by their connectivity and the higher mass (lower mobility) of the polymer backbone.

(56) $t_{MCP}$ was estimated from mass density of MCP, $d=1.07$ g cm$^{-3}$, molar mass of MCP, m=92 g mol$^{-1}$, and surface coverage of alkanethiol monolayers on gold a=4.7× $10^{14}$ molecules cm$^{-2}$ (Strong, L.; Whitesides, G. M., *Langmuir* 1988, 4, 546-558). $t_{MCP}$=am/(d $N_A$).

(57) Moulton, J., Gene Tools, *personal communication*.

(58) $t_P$=(4.9×10$^{12}$ chains cm$^{-2}$)(1×10$^{-14}$ cm$^2$ nm$^{-2}$)(20 nt chain$^{-1}$)(0.53 nm$^3$ nt$^{-1}$)=0.52 nm.

(59) A possible explanation for suppression of multivalent phosphate anions, as suggested by the model, is that the dielectric strength inside a probe layer is too low to stabilize multiply-ionized phosphate species.

(60) In the model, electrostatic and partitioning penalty energies (equation 5) combine such that a displacement in $V_{DC}$ can be compensated through adjustment of the $\beta_j$ coefficients. This degree of freedom was fixed by assuming $\beta_{Na+}$ =0 for the Morpholino monolayer.

(61) Although a three-layer model consisting of an MCP layer, unhybridized probes, and a solution-side layer of more solvated Morpholino-DNA hybrids might be more realistic, we continue to use two-layers as this was sufficient to reproduce experiment. Addition of a third, well-solvated and thus high capacitance layer would, in any case, exert a minor effect given that smaller capacitances dominate when arranged in series.

(62) Rant, U.; Arinaga, K.; Fujita, S.; Yokoyama, N.; Abstreiter, G.; Tornow, M., *Nano Lett.* 2004, 4, 2441-2445.

(63) $V_{DC}$ is assumed to not affect the dielectric constant.

(64) Prins, R.; Korswagen, A. R.; Kortbeek, A. G. T. G., *J. Organomet. Chem.* 1972, 39, 335-344.

(65) Popenoe, D. D.; Deinhammer, R. S.; Porter, M. D., *Langmuir* 1992, 8, 2521-2530.

(66) Laviron, E., *J. Electroanal. Chem.* 1974, 52, 355-393.

(67) Donnan, F. G., *J. Membr. Sci.* 1995, 100, 45-55.

(68) Naegeli, R.; Redepenning, J.; Anson, F. C., *J. Phys. Chem.* 1986, 90, 6227-6232.

(69) Homola, J.; Yee, S. S.; Gauglitz, G., *Sens. Actuators, B* 1999, 54, 3-15.

(70) Su, X. D.; Wu, Y. J.; Knoll, W., *Biosens. Bioelectron.* 2005, 21, 719-726.

(71) http://www.jobinwon.com/SPRi, http://www.g-sense.com.

(72) Sheikh, S.; Blaszykowski, C.; Thompson, M., *Anal. Lett.* 2008, 41, 2525-2538.

(73) Macanovic, A.; Marquette, C.; Polychronakos, C.; Lawrence, M. F., *Nucleic Acids Res.* 2004, 32, e 20.

(74) Uno, T.; Tabata, H.; Kawai, T., *Anal. Chem.* 2007, 79, 52-59.

(75) Aoki, H.; Tao, H., *Analyst* 2007, 132, 784-791.

(76) Zhu, L.; Lukeman, P. S.; Canary, J. W.; Seeman, N. C., *J. Am. Chem. Soc.* 2003, 125, 10178-10179.

(77) Liu, Y.; Wang, R.; Ding, L.; Sha, R.; Lukeman, P. S.; Canary, J. W.; Seeman, N. C., *Chem Bio Chem* 2008, 9, 1641-1648.

(78) Levine, P. M.; Gong, P.; Levicky, R.; Shepard, K. L., *IEEE J. Solid-State Circuits* 2008, 43, 1859-1871.

(79) Ghindilis, A. L.; Smith, M. W.; Schwarzkopf, K. R.; Roth, K. M.; Peyvan, K.; Munro, S. B.; Lodes, M. J.; Stover, A. G.; Bernards, K.; Dill, K.; McShea, A., *Biosens. Bioelectron.* 2007, 22, 1853-1860.

(80) Schienle, M.; Paulus, C.; Frey, A.; Hofmann, F.; Holzapfl, B.; Schindler-Bauer, P.; Thewes, R., *IEEE J. Solid-State Circuits* 2004, 39, 2438-2445.

(81) Takenaka, S.; Uto, Y.; Kondo, H.; Ihara, T.; Takagi, M., *Anal. Biochem.* 1994, 218, 436-443.

(82) Ihara, T.; Maruo, Y.; Takenaka, S.; Takagi, M., *Nucl. Acids. Res.* 1996, 24, 4273-4280.

(83) Brazill, S. A.; Kim, P. H.; Kuhr, W. G., *Anal. Chem.* 2001, 73, 4882-4890.

(84) Kutner, A.; Renstrom, B.; Schnoes, H. K.; DeLuca, H. F., *Proc. Natl. Acad. Sci. USA* 1986, 83, 6781-6784.

(85) Laviron, E., *J. Electroanal. Chem.* 1979, 100, 263-270.

(86) Popenoe, D. D.; Deinhammer, R. S.; Porter, M. D., *Langmuir* 1992, 8, 2521-2530.

(87) Prins, R.; Korswagen, A. R.; Kortbeek, A. G. T. G. *J. Organomet. Chem.* 1972, 39, 335-344.

What is claimed is:

1. A method to monitor the progress of hybridization of nucleic acid strands in solution with Morpholino strands, comprising:
   immobilizing the Morpholino strands on a conductive solid support in the form of a working electrode to form a Morpholino probe; and
   conducting in-situ, in real-time, label-free electrochemical measurements of the surface capacitance of the Morpholino probe,
   wherein the label-free electrochemical measurements are sensitive to hybridization-induced changes in the near-surface dielectric constant and charge organization of the Morpholino probe and comprise measurements of interfacial impedance derived from alternating charging current signals generated in response to application of an alternating potential perturbation between the conductive solid support and the nucleic acid solution.

2. The method as claimed in claim 1, wherein the nucleic acid is DNA.

3. The method as claimed in claim 2, wherein the electrochemical measurements comprise determination of hybridization-induced changes in the capacitance of the Morpholino probe.

4. The method as claimed in claim 1, further comprising immobilizing the Morpholino strands as a layer on the Morpholino probe, wherein the Morpholino layer is formed in a collapsed, desolvated state.

5. The method as claimed in claim 1, further comprising adding a 0.2 molar phosphate buffer to the nucleic acid solution, whereby the method is carried out at ionic strengths below that of the 0.2 molar phosphate buffer to improve sensitivity of detection of the progress of hybridization.

6. The method as claimed in claim 1, further comprising conducting the label-free electrochemical measurements at electrode potentials equal to or negative of the potential of an uncharged Morpholino probe layer so as to maximize the signal response.

7. The method as claimed in claim 1, wherein the hybridization results in a displacement of the charge in a positive direction, toward more positive potentials, thus allowing changes in potential of an uncharged Morpholino probe layer to be used as a metric of hybridization.

* * * * *